United States Patent [19]
Cesarini et al.

[11] Patent Number: 5,833,692
[45] Date of Patent: *Nov. 10, 1998

[54] SURGICAL INSTRUMENT

[75] Inventors: Peter M. Cesarini, Londonderry; Michael A. Fritschy, Derry; Karen Drucker, Danville, all of N.H.

[73] Assignee: Smith & Nephew, Inc., Andover, Mass.

[*] Notice: The term of this patent shall not extend beyond the expiration date of Pat. No. 5,620,447.

[21] Appl. No.: 630,497

[22] Filed: Apr. 10, 1996

Related U.S. Application Data

[63] Continuation of Ser. No. 534,743, Sep. 27, 1995, Pat. No. 5,620,447, which is a continuation of Ser. No. 200,662, Feb. 23, 1994, abandoned, which is a continuation-in-part of Ser. No. 11,364, Jan. 29, 1993, abandoned.

[51] Int. Cl.$^6$ .................................................. A61B 17/32
[52] U.S. Cl. .............................. 606/79; 606/170; 606/180
[58] Field of Search ............................... 606/79, 80, 81, 606/82, 83, 84, 85, 150, 167, 170; 128/751, 749, 752, 753, 754, 755; 604/22

[56] References Cited

U.S. PATENT DOCUMENTS

| | | |
|---|---|---|
| 274,096 | 5/1883 | Shutt . |
| 745,722 | 12/1903 | Freeman . |
| 1,630,239 | 5/1927 | Binkley et al. . |
| 1,636,636 | 7/1927 | Humble . |
| 2,878,809 | 3/1959 | Treace . |
| 3,342,175 | 9/1967 | Bulloch . |
| 3,618,611 | 11/1971 | Urban . |
| 3,847,154 | 11/1974 | Nordin . |
| 3,964,468 | 6/1976 | Schulz . |
| 4,020,847 | 5/1977 | Clark, III . |
| 4,167,943 | 9/1979 | Banko . |
| 4,167,944 | 9/1979 | Banko . |
| 4,203,444 | 5/1980 | Bonnell et al. . |
| 4,246,902 | 1/1981 | Martinez . |
| 4,258,716 | 3/1981 | Sutherland . |
| 4,265,231 | 5/1981 | Scheller, Jr. et al. . |
| 4,274,414 | 6/1981 | Johnson et al. . |

(List continued on next page.)

FOREIGN PATENT DOCUMENTS

| | | |
|---|---|---|
| 2074798 | 7/1992 | Canada . |
| 0 393 834 | 10/1990 | European Pat. Off. . |
| 0 445 918 | 9/1991 | European Pat. Off. . |
| 0 481 760 | 4/1992 | European Pat. Off. . |
| 0 538 984 | 4/1993 | European Pat. Off. . |
| 0 609 084 | 8/1994 | European Pat. Off. . |
| 0 613 661 | 9/1994 | European Pat. Off. . |
| 32 19 629 | 12/1983 | Germany . |
| U-86007100.9 | 9/1986 | Germany . |
| 38 28 478 | 5/1989 | Germany . |
| 61-265133 | 11/1986 | Japan . |
| 1 235 321 | 6/1971 | United Kingdom . |
| WO93/20760 | 10/1993 | WIPO . |

OTHER PUBLICATIONS

European Search Report Dated Jul. 01, 1991.
Palmaz, J.C. et al., "Atherosclerotic Rabbit Aortas: Expandable Intraluminal Grafting", Radiology, vol. 160, No. 3, Sep. 1986, pp. 723–726.
United States Surgical Corporation Advertisement, Auto Suture™ Stapleoscopy™ endoscopic instruments, Journal of Laparoendoscopic Surgery, 1992.

*Primary Examiner*—Guy V. Tucker
*Attorney, Agent, or Firm*—Fish & Richardson P.C.

[57] ABSTRACT

A surgical instrument comprises a first member extending distally from a proximal end and having an opening in a distal region for admitting tissue, and a second member disposed within the first member for moving a cutting implement and causing it to cut tissue that is exposed to the implement through the opening. A knob is attached to the proximal end of the first member and is mounted in rotatable engagement with a hub of the instrument to rotate the first member and selectively change a rotational orientation of the opening with respect to the hub. The knob is axially movable with respect to the hub to a locked position in which the knob nonrotatably engages the hub.

17 Claims, 15 Drawing Sheets

U.S. PATENT DOCUMENTS

| | | |
|---|---|---|
| 4,320,761 | 3/1982 | Haddad . |
| 4,433,687 | 2/1984 | Burke et al. . |
| 4,440,170 | 4/1984 | Golden et al. . |
| 4,466,429 | 8/1984 | Loscher et al. . |
| 4,483,562 | 11/1984 | Schoolman . |
| 4,512,344 | 4/1985 | Barber . |
| 4,517,977 | 5/1985 | Frost . |
| 4,522,206 | 6/1985 | Whipple et al. . |
| 4,541,423 | 9/1985 | Barber . |
| 4,545,374 | 10/1985 | Jacobson . |
| 4,576,772 | 3/1986 | Carpenter . |
| 4,589,412 | 5/1986 | Kensey . |
| 4,631,052 | 12/1986 | Kensey . |
| 4,632,110 | 12/1986 | Sanagi . |
| 4,644,951 | 2/1987 | Bays . |
| 4,646,738 | 3/1987 | Trott . |
| 4,649,919 | 3/1987 | Thimsen et al. . |
| 4,662,371 | 5/1987 | Whipple et al. . |
| 4,669,471 | 6/1987 | Hayashi . |
| 4,674,501 | 6/1987 | Greenberg . |
| 4,681,106 | 7/1987 | Kensey et al. . |
| 4,690,140 | 9/1987 | Mecca . |
| 4,696,667 | 9/1987 | Masch . |
| 4,705,038 | 11/1987 | Sjostrom et al. . |
| 4,706,655 | 11/1987 | Krauter . |
| 4,738,256 | 4/1988 | Freeman et al. . |
| 4,739,762 | 4/1988 | Palmaz . |
| 4,760,848 | 8/1988 | Hasson . |
| 4,763,669 | 8/1988 | Jaeger . |
| 4,770,174 | 9/1988 | Luckman et al. . |
| 4,834,729 | 5/1989 | Sjostrom . |
| 4,842,578 | 6/1989 | Johnson et al. . |
| 4,858,897 | 8/1989 | Irifune . |
| 4,867,155 | 9/1989 | Isaacson . |
| 4,880,015 | 11/1989 | Nierman . |
| 4,945,920 | 8/1990 | Clossick . |
| 4,950,273 | 8/1990 | Briggs . |
| 4,982,727 | 1/1991 | Sato . |
| 4,986,825 | 1/1991 | Bays et al. . |
| 4,998,527 | 3/1991 | Meyer . |
| 5,094,247 | 3/1992 | Hernandez et al. . |
| 5,147,373 | 9/1992 | Ferzli . |
| 5,152,744 | 10/1992 | Krause et al. . |
| 5,174,300 | 12/1992 | Bales et al. . |
| 5,217,479 | 6/1993 | Shuler . |
| 5,282,821 | 2/1994 | Donahue . |
| 5,290,308 | 3/1994 | Knight et al. . |
| 5,330,502 | 7/1994 | Hassler et al. . |
| 5,376,078 | 12/1994 | Dinger III et al. . |
| 5,620,447 | 4/1997 | Smith et al. .............................. 606/79 |

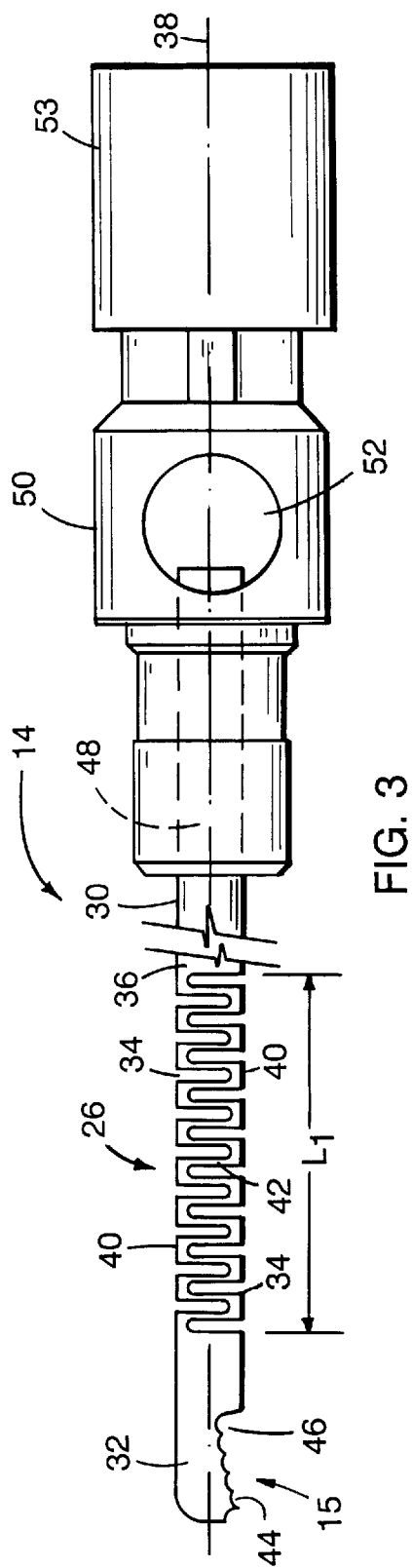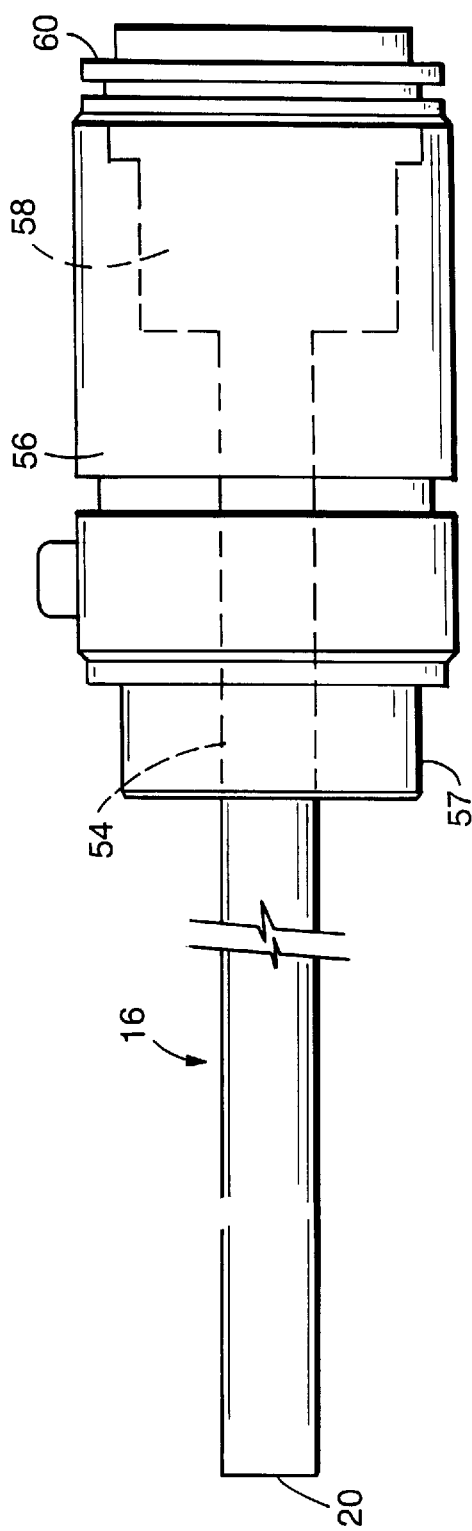

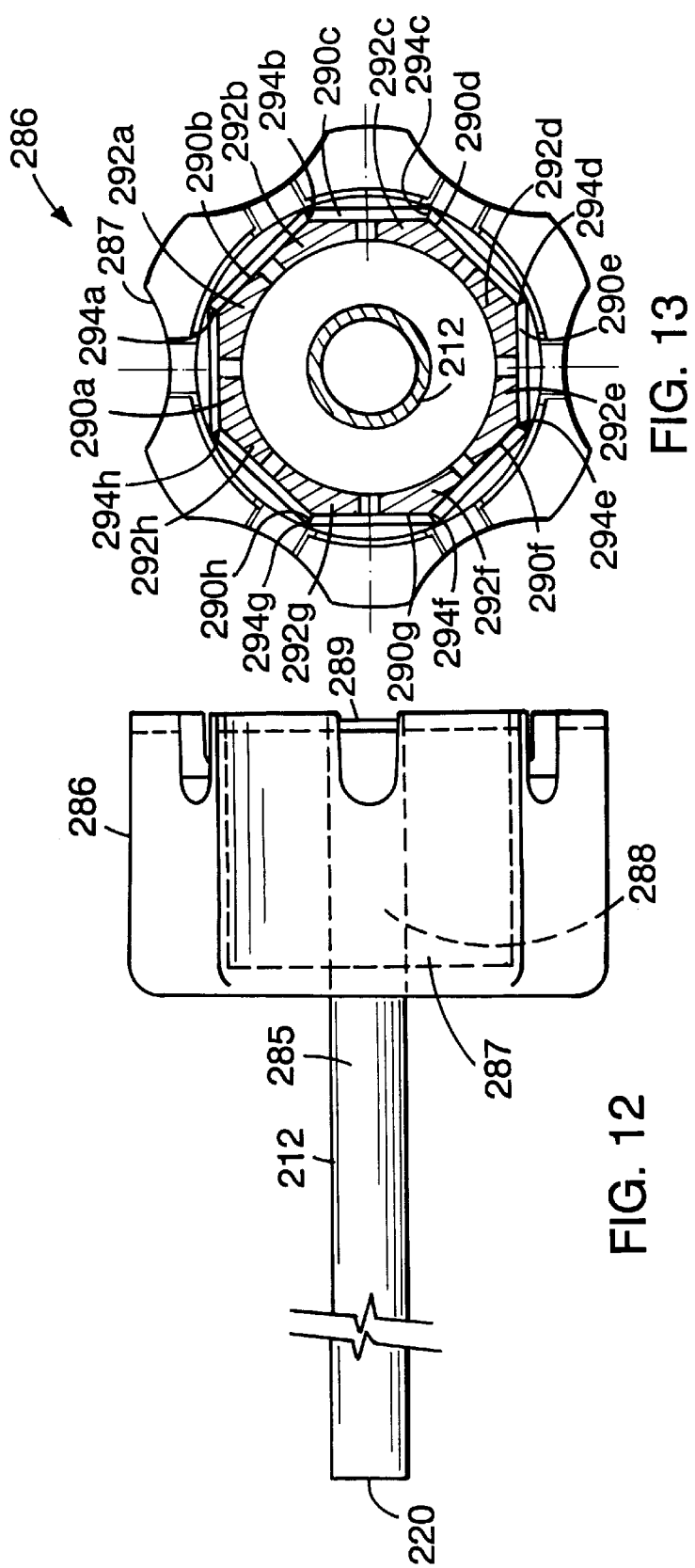

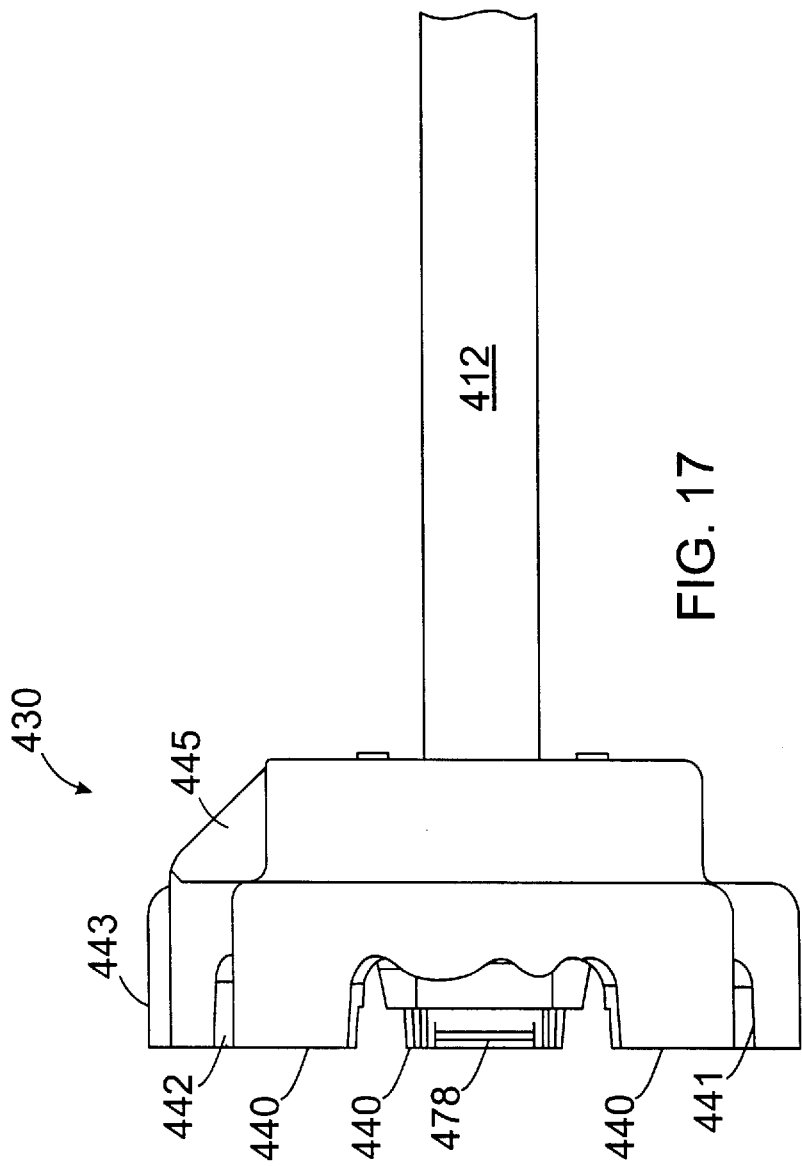

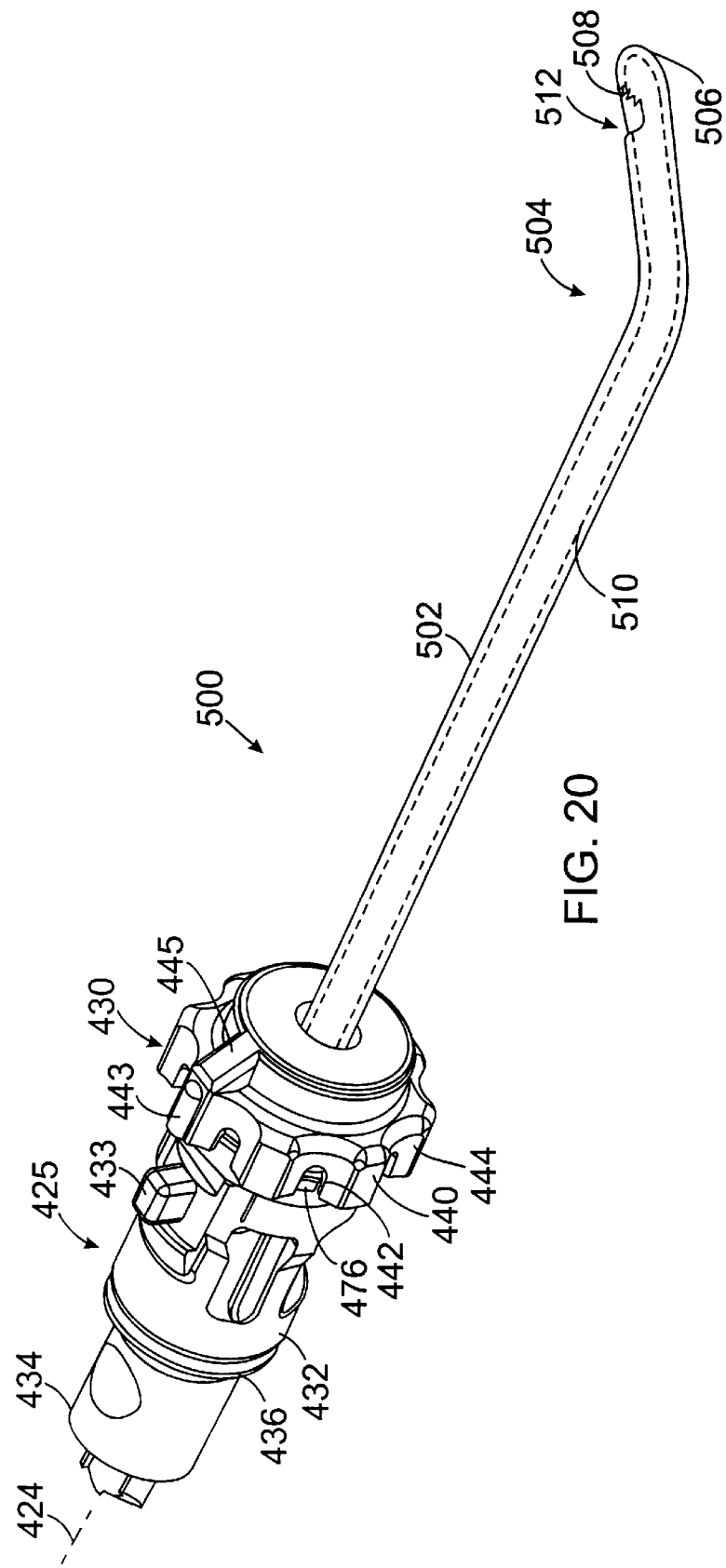

SURGICAL INSTRUMENT

CROSS REFERENCE TO RELATED APPLICATIONS

This application is a continuation-in-part of patent application Ser. No. 08/534,743, filed Sep. 27, 1995, now U.S. Pat. No. 5,620,447, which is a continuation of Ser. No. 08/200,662, filed Feb. 23, 1994, now abandoned, which is a continuation-in-part of application Ser. No. 08/011,364, filed Jan. 29, 1993, now abandoned, which is related to an application entitled "Surgical Instrument," filed the same day as the parent application, assigned to the present assignee, and incorporated herein by reference.

BACKGROUND OF THE INVENTION

This invention relates to surgical instruments, and in particular to powered arthroscopic surgical instruments.

Powered arthroscopic surgical instruments typically include a rigid, stationary outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument. Examples of such surgical instruments are described in U.S. Pat. Nos. 4,203,444, 4,274,414, 4,834,729, and 4,842,578, all of which are assigned to the present assignee.

Some arthroscopic surgical instruments are linear, that is, straight between their proximal and distal ends. Others are curved to facilitate positioning the cutting implement against tissue to be cut without requiring that the instrument be removed from the body and reinserted through an additional puncture. In a curved instrument, a region of the inner tube is flexible to enable the inner tube to accept the curvature imposed by the outer tube while transmitting the torsion applied by the motor to the blade. In both cases, the user changes the orientation of the cutting implement by rotating the instrument.

SUMMARY OF THE INVENTION

This invention features a surgical instrument which enables a user to temporarily lock a rotatable component in a selected orientation with respect to a hub of the instrument. When desired, the instrument can be "unlocked" to return the component to its rotatable condition. Among other advantages, the invention provides a simple yet reliable way of guarding against accidental movement of the component during surgery when fixed positioning is desired.

In one general aspect of this concept, the rotatable component is a tissue-admitting opening in a distal region of a first member of the instrument, and a knob attached to a proximal end of the first member is mounted in rotatable engagement with the hub to rotate the first member and selectively change a rotational orientation of the opening with respect to the hub, and is axially movable with respect to the hub to a locked position in which the knob nonrotatably engages the hub; tissue admitted through the opening is cut by a cutting implement which is moved by a second member disposed within the first member.

Preferred embodiments include the following features.

The knob is axially movable in an opposite direction from the locked position to restore the rotatable engagement between the knob and the hub. The hub includes one or more protrusions which are axially spaced from corresponding portions of the knob when the knob is in rotatable engagement with the hub. The protrusions are disposed to engage the portions of the knob when said knob is axially moved to the locked position.

In one embodiment, the knob comprises a plurality of members circumferentially spaced to define an opening in which a portion of the hub is disposed. The hub includes a pair of protrusions spaced by the width of the members so that one of member is positioned between the pair of protrusions when the knob is axially moved to the locked position. Preferably, multiple pairs of like-spaced protrusions are provided.

Each member includes a notch configured to receive a protrusion when the knob is axially moved to the locked position. This enhances the fit between the protrusions and the members, and provides additional security against accidental rotation.

The knob is mounted so that the knob can be selectively rotated to a plurality of discrete positions while remaining in interengagement with the hub. As a result, the opening can be selectively positioned at a corresponding plurality of discrete rotational orientations. The hub includes a plurality of flexible cantilevered fingers each of which corresponds to one of the discrete positions. Each one of a plurality of mating regions on the knob engages one of the fingers during rotation of the knob to maintain the selective positioning of the opening.

A ridge disposed on the exterior surface of the hub is engaged by a resilient member on the knob when the knob is axially moved to the locked position. For example, this engagement is provided by the above-discussed circumferentially spaced members. The ridge is circumferentially arranged around the portion of the hub received within the opening of the knob. Each resilient member includes a radial projection which engages the ridge when the knob is axially moved to the locked position.

A second annular ridge may be arranged around the portion of the hub and axially spaced from the first mentioned ridge. In such an implementation, the radial projections of the resilient members are axially disposed between the ridges when the knob is in rotatable engagement with the hub.

In one embodiment, first member includes a bend region that angularly offsets the opening from an axis of the first member. The second member has a flexible region disposed in the bend region to transmit force applied at a proximal end of the second member through the bend region to move the cutting implement.

In another aspect of the invention, the rotatable (and lockable) component is a bend region of the instrument. The instrument includes a first member extending distally from a proximal end and having a bend region that angularly offsets a distal end of the first member from an axis, and a second member having a proximal end mounted to a hub and extending coaxially with the first member to a distal end disposed distally of said bend region. The tissue-admitting opening is at the distal end of the second member and admits tissue for cutting by a cutting implement movable with respect to the second member. A knob is attached to the proximal end of the first member and is mounted in rotatable engagement with the hub to rotate the first member and selectively change a rotational orientation of said bend region with respect to the hub, and the knob is axially movable with respect to the hub to a locked position in which the knob nonrotatably engages the hub.

Preferred embodiments include the following additional features.

The second member includes a flexible region in the bend region of the first member. In one embodiment, the second member is disposed within the first member and extends through an open distal end of the first member. In another embodiment, the first member is disposed within the second member. In either embodiment, a third member may be disposed coaxially with the first and second members and operatively connected to move the cutting implement. The third member includes a flexible region in the bend region.

The invention provides all of the advantages of a rotatable instrument (discussed in the above-identified parent applications) while also giving the user the ability to temporarily lock—and subsequently release—the rotatable component in any desired rotational position.

Other features and advantages of the invention will become apparent from the following detailed description, and from the claims.

BRIEF DESCRIPTION OF THE DRAWINGS

FIGS. 3–5 show inner, intermediate, and outer tubes, respectively, of the surgical instrument of FIG. 1.

FIGS. 10–12 show inner, intermediate, and outer tubes, respectively, of the surgical instrument of FIG. 8.

FIG. 13 is a cross-section of the surgical instrument, taken along line 6—6 of FIG. 9.

FIGS. 16 and 17 show intermediate, and outer tubes, respectively, of the surgical instrument of FIG. 15.

FIG. 20 shows yet another embodiment of a surgical instrument according to the invention.

DESCRIPTION OF PREFERRED EMBODIMENTS

Figure 1:
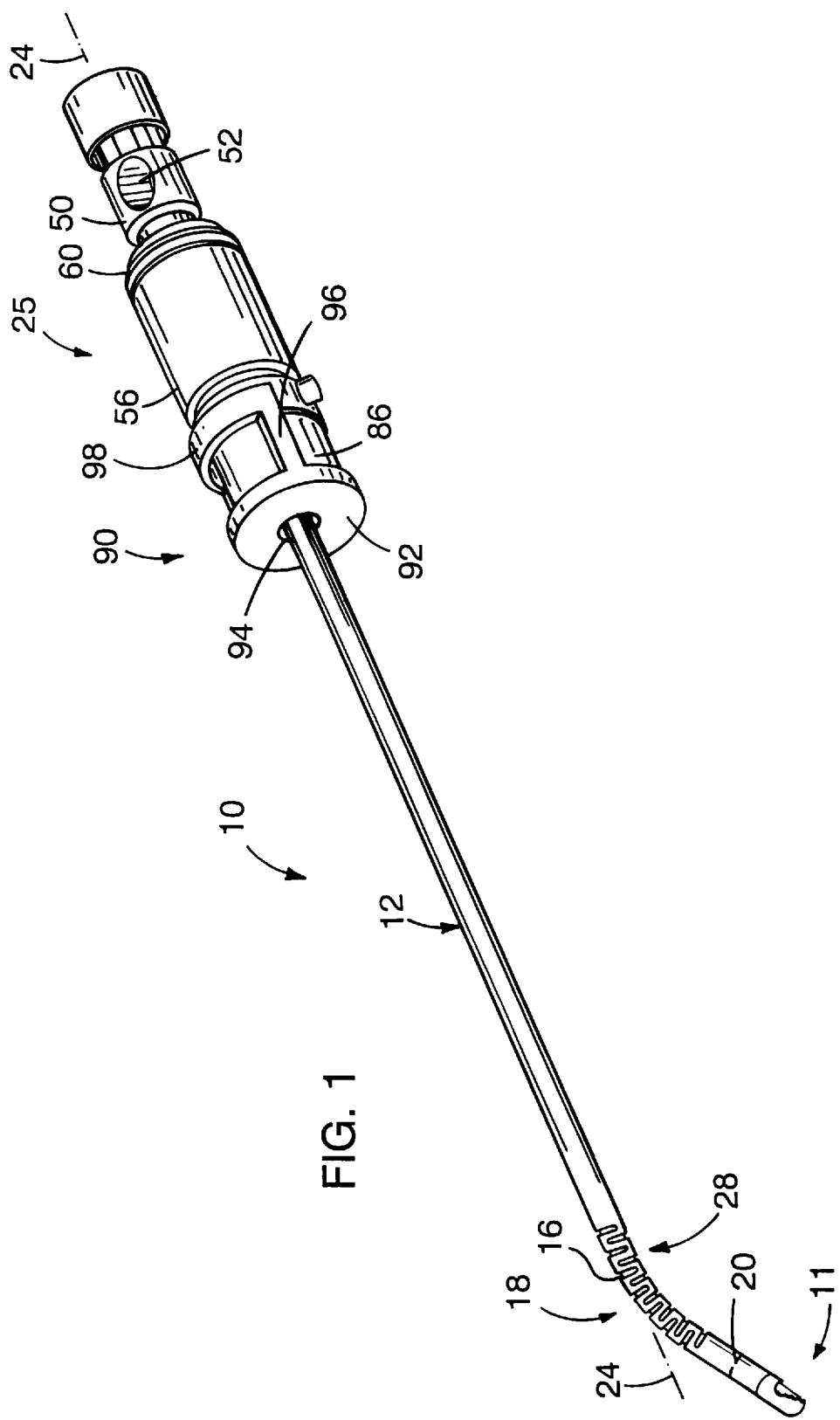
FIG. 1 shows a surgical instrument according to the invention, having a cutting implement that is adjustable to different rotational positions.
Figure 2:
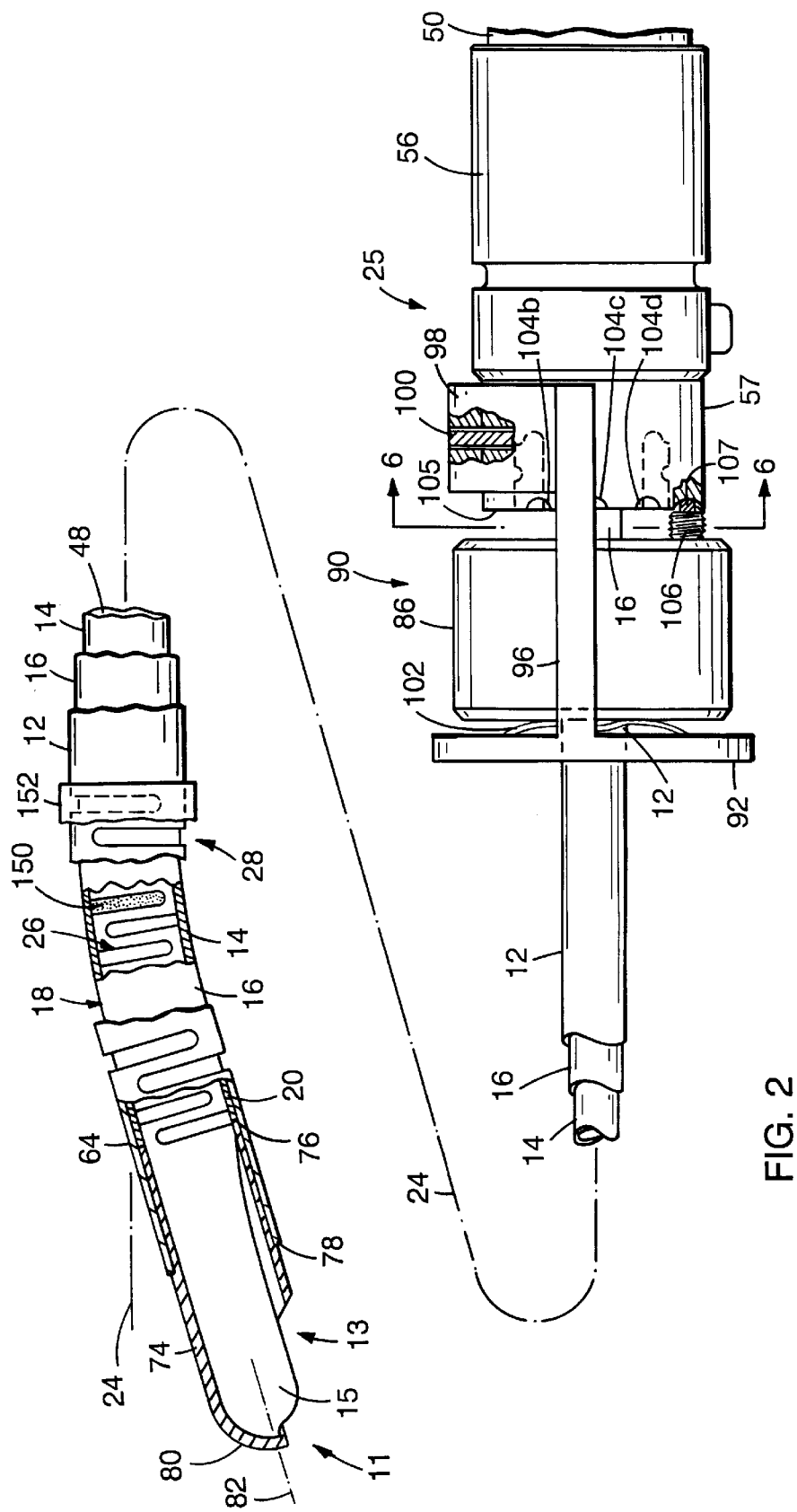
FIG. 2 is a partial cross-sectional view of portions of the instrument of FIG. 1, showing details of the tip and base.

Referring to FIGS. 1 and 2, surgical instrument 10 suitable for performing, e.g., closed, arthroscopic surgery on the knee with a surgical tool 11, includes an outer tube 12 within which a rotating inner tube 14 is coaxially disposed. The distal end of outer tube 12 includes an opening 13, the edges of which are sharpened and serrated, through which a cutting implement 15 (formed by sharpened, serrated edges of a similar opening in the distal end of inner tube 14) of surgical tool 11 is periodically exposed as inner tube 14 rotates. A rigid, stationary intermediate tube 16 is disposed coaxially between outer tube 12 and inner tube 14. Intermediate tube 16 is curved through a bend region 18 disposed slightly proximally of the distal end 20 of tube 16 to angularly offset surgical tool 11 from a generally straight axis 24 of surgical instrument 10. Bend region 18 enables surgical instrument 10 to operate on surgical areas that are difficult to reach with a straight instrument.

Tubes 12, 14, and 16 are proximally supported by a base 25. As discussed in detail below, inner tube 14 includes a slotted, flexible region 26 disposed within bend region 18 to accept the curvature imposed by bend region 18 and transmit torque (and other forces) applied at base 25 through bend region 18 to rotate cutting implement 15 with sufficient force to sever tissue or other body material exposed through opening 13. Outer tube 12 has a slotted, flexible region 28 that envelopes bend region 18 and allows the user to rotate outer tube 12 with respect to base 25, despite the curvature imposed by bend region 18. This feature enables the user to selectively change the rotational orientation of opening 13—and hence surgical tool 11—with respect to axis 24 without rotating the entire surgical instrument 10, and thus without changing the orientation of bend region 18 and the angular offset that it provides. As a result, the user can maintain surgical instrument 10 in an essentially fixed position, while changing the angle of attack of cutting implement 15 by rotating outer tube 12.

Referring also to FIG. 3, inner tube 14 is made from metal, such as stainless steel, and has rigid proximal and distal regions 30, 32, that are connected by flexible region 26. Flexible region 26 is relieved with an axially extending series of circumferential slots 34 disposed in the walls 36 of tube 14 and is continuous with the adjacently disposed proximal and distal regions 30, 32. (Slotting a rotatable tube for flexibility is described in a copending application entitled "Surgical Instrument," Ser. No. 07/634,599, now U.S. Pat. No. 5,152,744, filed on Dec. 27, 1990, assigned to the present assignee and incorporated herein by reference.) Slots 34 are perpendicular to the longitudinal axis 38 of tube 14 and are arranged in a symmetrical pattern along the length $L_1$ of flexible region 26 to provide uniform flexibility and avoid any substantial deviation in flexibility as inner tube 14 rotates. This minimizes torsional stresses on inner tube 14 and helps prolong the operating life of surgical instrument 10.

Slots 34 are disposed parallel to each other (vertically in FIG. 3) along length $L_1$. Adjacent slots 34 extend into tube 14 from opposite directions (e.g., from above and below tube 14 in FIG. 3) and are circumferentially offset from each other by 180°. The number of slots 34, their dimensions (i.e., their width and depth), and the spacing between adjacent slots are a function of the desired degree of flexibility. For example, the width of each slot 34 and the spacing between slots 34 each are 0.020 inches (0.508 mm).

A tab 40 bounds each slot 34 circumferentially, and adjacent tabs 40 are interconnected by annular rings 42, which provide the spacing between adjacent slots 34. The interconnected series of rings 42 and tabs 40 provide a series of interconnected, integrally formed "U" shaped leaf springs along the length $L_1$ of flexible region that give uniform flexibility and efficiently transmit torque (i.e., rotational force) applied at proximal region 30 of tube 14 to distal region 32 through the curvature imposed by bend region 18 (FIG. 1). The depth of slots 34 (i.e., the amount by which slots 34 extend radially into tube 14) is a function of the desired torsional strength of flexible region 26. For example, slots 34 have a depth of about 75% of the outer diameter (0.135 inches, or 3.429 mm) of inner tube 14.

The length $L_1$ of flexible region 26 is a function of the length of bend region 18. Flexible region 26 should be sufficiently long (e.g. 0.70 inches, or 17.78 mm) so as to span the entire length of bend region 18, with adjacent rigid regions 30, 32 lying within straight regions of stationary intermediate tube 16. This allows flexible region 26 to make a smooth transition between the straight regions of intermediate tube 16 and bend region 18, thereby reducing stresses imposed by the curved inner walls of bend region on walls 36 of inner tube 14.

Flexible region 26 can be formed by any suitable method. Examples include wire EDM (electric discharge machining) and sawing. Both are described in the aforementioned U.S. patent application Ser. No. 07/634,599, now U.S. Pat. No. 5,152,744.

Distal region 32 of inner tube 14 supports cutting implement 15 (which is, for example, stainless steel and attached to tube 14 by welding or brazing). Cutting implement 15 is defined by serrated, sharpened edges 44 of a distal opening 46 in tube 14 and is sized to provide a close running fit with the distal end of outer tube 12 for efficient cutting. Opening 46 is an extension of a central aperture 48 in inner tube that runs the entire length of tube 14.

Proximal region 30 of inner tube 14 is rigidly mounted to a drive shaft 50 that rotates within base 25. Central aperture 48 terminates in a vacuum source opening 52 in drive shaft 50. The proximal end 53 of drive shaft 50 fits into a handpiece 110 (FIG. 7), which includes a motor 112 for rotating drive shaft 50 and inner tube 14 with respect to tubes 12, 16. One example of such a handpiece is described in U.S. Pat. No. 4,705,038, entitled "Surgical System for Powered Instruments", and assigned to the present assignee, which is incorporated by reference. Opening 52 is coupled to a vacuum source 114 (FIG. 7) during operation to remove severed tissue and irrigating fluid from the surgical site via aperture 48 in a manner described in detail below.

FIG. 4 shows intermediate tube 16 (before bend region 18 is formed), which is made from a rigid material such as metal (e.g., stainless steel). Intermediate tube 16 is hollow along its entire length to provide a passage 54 that receives inner tube 14, which protrudes through the open distal end 20 of intermediate tube 16 (FIG. 2). The inner diameter of intermediate tube 16 is only slightly larger than the outer diameter of inner tube 14 (e.g., by approximately 0.002 inches, or 0.051 mm); this allows inner tube 14 to rotate freely but helps minimize wobbling of tube 14 to keep the sharp cutting edges of implement 15 and opening 13 closely aligned.

The proximal end of intermediate tube 16 is rigidly mounted to a hub 56 of base 25. A cavity 58 in hub 56 communicates with passage 54 and is configured to receive drive shaft 50. During assembly, inner tube 14 is inserted through hub 56 into intermediate tube 16 (before bend region 18 is formed). A pliable fitting 60 retains drive shaft 50 within hub 56. Fitting 60 provides a fluid-tight seal when base 25 is inserted into handpiece 110.

Figure 5:
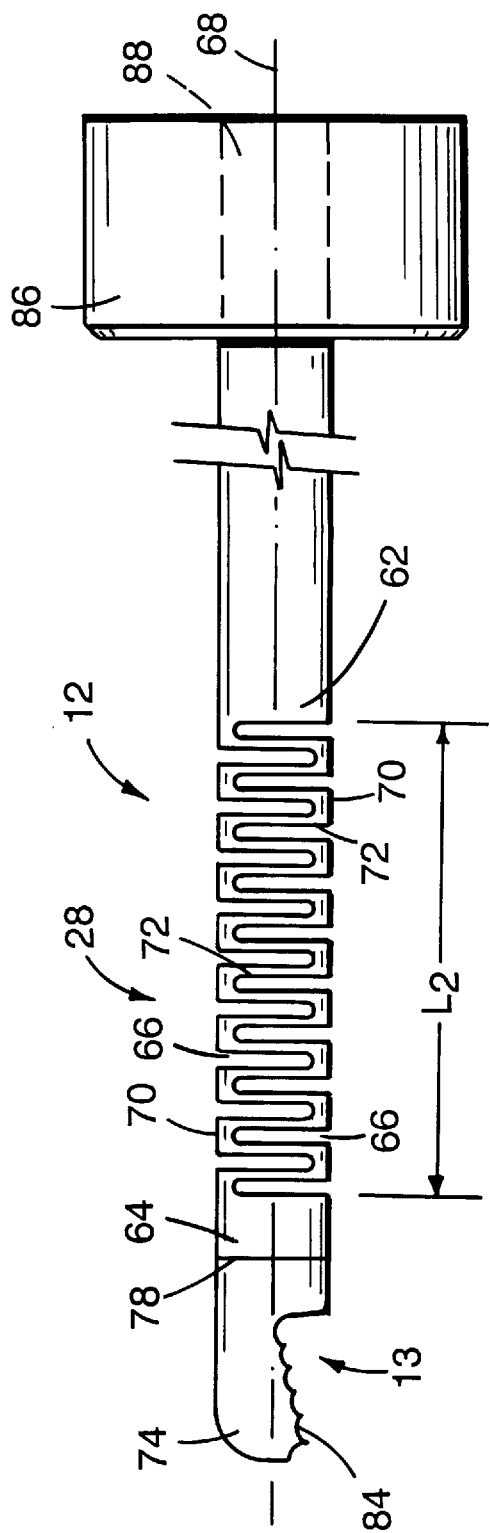

Referring to FIG. 5, outer tube 12 is essentially a larger version of inner tube 14 and includes rigid proximal and distal regions 62, 64 that are integrally connected by flexible region 28. Flexible region 28 includes an axially extending series of slots 66 disposed perpendicularly to the longitudinal axis 68 of tube 12 and arranged in a symmetrical pattern along the length $L_2$ of flexible region 28. Adjacent slots 66 extend radially into tube 12 in opposite directions (i.e., from above and below tube 12 in FIG. 5). Each slot 66 is approximately 0.025 inches (0.635 mm) wide and has a depth of about 0.140 inches (3.556 mm).

Each slot 66 is bounded by a tab 70. Adjacent tabs 70 are circumferentially offset by 180° and are connected by rings 72 (each of which has the same width as slots 66) to form a series of "U" shaped springs that are continuous with each other and with proximal and distal regions 62, 64. As a result, flexible region 28 is both sufficiently pliable to accept the curvature imposed by bend region 18 and sufficiently torsionally stiff to transmit applied rotational force through bend region 18 to rotate opening 13. Length $L_2$ should be such that flexible region 28 spans the entire length of bend region 18, with the adjacently-disposed rigid portions 62, 64 of outer tube being aligned with straight portions of intermediate tube 16.

As shown most clearly in FIG. 2, to ensure a close running fit between sharp edges 44 of cutting implement 15 and the corresponding cutting edges 84 of opening 13 despite the spacing between tubes 12, 14 that intermediate tube 16 provides, a distal extension 74 having the same inner diameter as intermediate tube 16 is secured to outer tube 12 at distal end 64. Extension 74 is, e.g., stainless steel, and is welded or brazed to outer tube 12, which can be a softer material, such as aluminum. The proximal end of extension 74 has a reduced outer diameter to allow it to be disposed within outer tube 12 and abut intermediate tube 16 at joint 76. A shoulder 78 on distal extension 74 limits the amount by which extension 74 is inserted into distal end 64 during assembly.

Opening 13 is disposed in a distal tip 80 of extension 74 and faces somewhat to the side of outer tube 12. That is, opening 13 does not extend completely to the centerline 82 of extension 74. As a result, while surgical tool will cut tissue that enters opening 13 from the distal end of instrument 10, the majority of the cutting action is to one side. Moreover, tip 80 provides distal support for the rotating inner tube 14. The edges 84 of opening 13 are sharpened and serrated to cooperate with sharp edges 44 of cutting implement 15. The clearance between inner tube 14 and the inner diameter of outer tube extension 74 and intermediate tube 16 is small (e.g., approximately 0.002 inches, or 0.051 mm) to maintain the close running fit between edges 44, 84 while allowing inner tube 14 to rotate freely. The identical inner diameters of extension 74 and intermediate tube 16 avoid inner tube 14 scoring or seizing as it rotates.

Proximal region 62 (FIG. 5) of outer tube 12 is rigidly secured to a drum 86 at a sealed joint. Drum 86 serves as a knob to enable the user to manually rotate tube 14, and is rotatably mounted to base 25 in a manner described below. A central passage 88 extends through outer tube 12 and drum 86 to receive intermediate tube 16 and inner tube 14. The inner diameter of outer tube 12 (proximally of extension 74) only slightly exceeds the outer diameter of intermediate tube 16 (e.g., by approximately 0.002 inches, 0.051 mm). This allows the user to rotate outer tube 12 but avoids excessive play between tubes 12, 16.

Referring to FIG. 2, outer tube 12 and drum 86 are rotatably mounted to base 25 with a spring-loaded rotation assembly 90. Drum 86 is captured between the distal end 57 of hub 56 and a faceplate 92, which includes an opening 94 (FIG. 1) through which outer tube 12 projects. A pair of axially extending bars 96 connect faceplate 92 to a sleeve 98 that is rigidly mounted to hub distal end 57 by one or more press-fit pins 100. A spring 102 (e.g., a wave washer), which fits within a recess (not shown) in faceplate 92, resiliently biases drum 86 toward hub 56.

Figure 6:
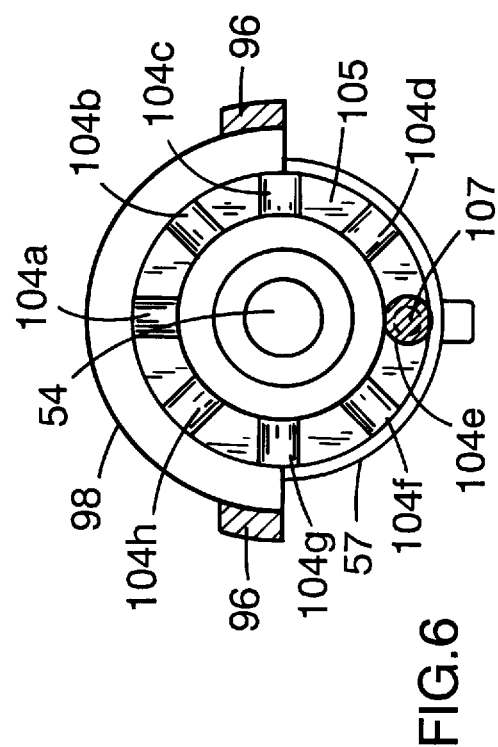
FIG. 6 is a cross-section of the base of the surgical instrument, taken along line 6—6 of FIG. 2.

Referring also to FIG. 6 (which, for clarity does not show tubes 14, 16 in cross-section), distal end 57 of hub 56 includes a series of (such as eight) rounded recesses 104a–104h disposed in an annular surface 105 of hub 56 that faces drum 86. Recesses 104a–104h are spaced by equal amounts (such as by 45°) around the circumference of hub 56. Surface 105 is flat between adjacent recesses 104a–104h. A plunger 106 having a spring-loaded, ball shaped tip 107 is threaded into drum 86. Tip 107 is resiliently urged against hub 56 and into a selected one of recesses 104a–104h by spring 102.

Thus, the user can selectively rotate drum 86—and hence outer tube 12 and surgical tool opening 13—to one of eight discrete rotational orientations. The biasing provided by spring 102 maintains plunger tip 107 in the selected recess 104a–104h to avoid accidental rotation. As drum 86 is rotated between recesses 104a–104h, tip 107 is compressed into plunger 106 by flat surfaces 105. Recesses 104a–104h are arranged to allow opening 13 to be rotated in a ratchet-like fashion to commonly used positions with respect to axis 24. For example, positioning plunger tip 107 in recess 104a orients opening 13 oppositely from the direction of curvature of bend region 18 (FIG. 2), that is, upwardly. With plunger 106 moved to recess 104e, opening 13 is aligned with the curvature direction and is oriented downwardly (the position shown in FIG. 2). Similarly, recesses 104c and 104g correspond to left and right orientations. Recesses 104b, 104d, 104f, and 104h provide intermediate positions for opening 13.

Figure 7:
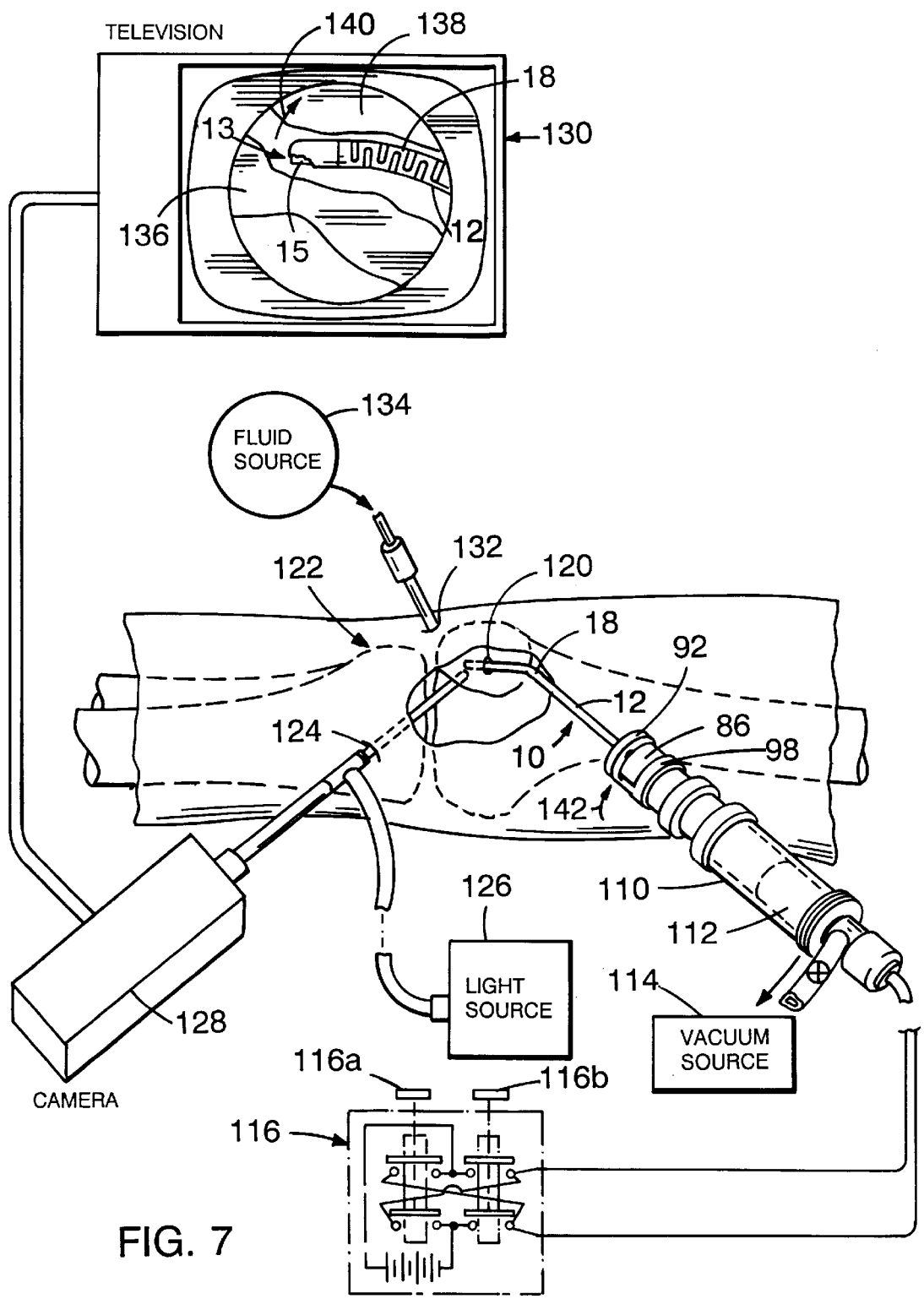
FIG. 7 shows the surgical instrument of FIG. 1 in use.

Referring also to FIG. 7, in operation, surgical instrument 10 is inserted into the distal end of a handpiece 110 and is introduced as shown through a puncture wound 120 into the knee joint 122, below the patella. Light is projected into the joint via a second puncture 124 using a fiber optic light source 126, and a visual image of the surgical site is returned through a separate optical path to a television camera 128. The image is delivered by camera 128 onto a television screen 130 for viewing by the surgeon. (Alternatively, the surgeon can view the image using an eyepiece, or the image can be recorded.)

The surgeon operates surgical tool 11 by activating motor 112, which receives operating potential and current from power supply 116. Motor 112 engages and rotates drive shaft 50, thereby applying rotational force to inner tube 14 and rotating tube 14 with respect to tubes 12, 16. The surgeon controls rotational speed and direction (either unidirectional or oscillatory) using foot switches 116a, 116b, which control the magnitude and polarity of operating potential and current provided by power supply 116 to motor 112. Motor 112 is capable of rotating inner tube 14 over a wide range of speeds, e.g., between about 100 rpm and 5000 rpm, and can deliver a torque of up to 25 oz. inches (0.177 Nm).

Different types of surgical instruments such as instrument 10 have rotational and torsional limits. To prevent the surgeon from inadvertently operating instrument 10 at dangerously high speeds and torques, instrument 10 identifies to sensors (not shown) in handpiece 110 what type of instrument it is, and the speed of and torsion applied by motor 112 is controlled so that these limits are not exceeded. (This control technique is described in the aforementioned U.S. Pat. No. 4,705,038.)

The torsion that motor 112 provides is efficiently delivered to cutting implement 15 by flexible region 26. Although region 26 is sufficiently flexible to accept the curvature imposed by bend region 18, it has a high degree of torsional stiffness and thus provides good torque response. That is, torsion applied by motor 112 is transmitted to distal region 32 of inner tube 14 substantially immediately when inner tube 14 is rotated from its rest position, without requiring any significant "preloading" of flexible region 26 prior to passing the torque to distal end 32. Also, flexible region 26 does not expand in diameter by any significant amount as it rotates and applies torque to distal end 32, reducing the possibility that tube 14 will bind within intermediate tube 16 during rotation.

During the surgical procedure, the body joint is distended with fluid introduced through a third puncture wound 132 from a fluid source 134. The fluid irrigates the site and renders tissue 136 (which is, e.g., synovial tissue) mobile so that it floats and can be displaced (similar to the movement of seaweed in water). Note that synovial tissue 136 is located beneath outer tube 12; thus, drum 86 is positioned so that plunger 106 is in recess 104e (FIGS. 2 and 6). The curvature provided by bend region 18 allows surgical instrument 10 to be easily positioned to place surgical tool 11 against tissue 136 (even if tissue 136 is located in a region of the joint that cannot easily be reached by a straight instrument) without manipulating instrument 10 unduly or requiring that additional punctures be made to gain access to tissue 136. This reduces patient discomfort, as well as the chances for infection and other deleterious consequences of the surgery.

The surgeon progressively cuts away synovial tissue 136 by moving surgical instrument 10 from side to side and in the axial direction using handpiece 110 (while viewing television screen 130). If during the procedure the surgeon wishes to cut tissue from another region of the synovial tissue, such as region 138 located above outer tube 14, the present invention allows him to do so simply by changing the rotational orientation of surgical tool opening 13 (e.g., in the direction of arrow 140) while maintaining handpiece 110 in a fixed position—that is, without requiring the surgeon to rotate or pivot handpiece 110.

This is accomplished, for example, by grasping drum 86 with the finger and thumb of one hand (while the other hand continues to grasp the body of handpiece 110) and turning drum 86 in the direction in which opening 13 is selected to rotate (e.g., along arrow 142). The rotational force applied by the surgeon is transmitted through bend region 18 by flexible region 28, thereby causing distal extension 74 of outer tube 12 to rotate with respect to intermediate tube 16 and base 25 and change the orientation of opening 13 with respect to axis 24 (in this case, by 180°).

In this example, in which tissue 138 is located above outer tube 12, the surgeon continues to rotate drum 86 until plunger 106 rests within recess 104a. As drum 86 is rotated between recesses, plunger 106 slides across flat surface 105 and drum 86 compresses spring 102 against faceplate 94. Thus, spring 102 positively urges plunger 106 into each recess 104 as it is encountered, thereby giving the surgeon kinesthetic feedback as to the amount by which opening 13 has been rotated.

The surgeon can change the rotational orientation of opening 13 at any time. For example, inner tube 14 can be driven by motor 112 or may be stationary while the surgeon rotates opening 13. Distal extension 74 rotates smoothly with respect to the stationary intermediate tube 16 at joint 76, while providing constant distal support (at tip 80) for rotating inner tube 14. The identical inner diameters of tube 16 and extension 74 help ensure that the rotation of outer tube 12 does not cause inner tube 14 to bind or seize. The surgeon can return to cutting tissue 136 at any time simply by rotating drum 86, either in the opposite direction from arrow 142 or in the same direction to trace a 360° arc from his starting point.

Tissue fragments and other body material cut by surgical tool 11 are withdrawn from the surgical site along with irrigation fluid via central aperture 48 of inner tube 14 (FIG. 2) in response to suction applied by vacuum source 114. Note that as flexible region 26 rotates within the bend region 18, the width of each slot 34 at the periphery of tube wall 36 progressively increases and decreases incrementally with respect to its nominal width. This is because flexible region 26 tends to stretch at the apex of bend region 18 (i.e., the upper part of bend region 18 in FIG. 2) and compress at the base of the bend. This alternating widening and constricting as tube 14 rotates may generate turbulence in the fluid being withdrawn through aperture 48, thereby assisting in the transport of tissue fragments through the chamber and out of surgical instrument 10.

The exposure of aperture 48 to the interior walls of intermediate tube 16 through slots 34 has not been found to allow tissue fragments to become caught in the slots and cause blockage, perhaps due to the small width of the slots and the continual rotation of inner tube 14. Fluid likewise has not been found to seep between tubes 14, 16 via slots 34 (or between tubes 12, 16) in amounts that interfere with the operation of instrument 10.

Other embodiments are within the scope of the following claims.

For example, although surgical instrument 10 is shown with bend region 18 oriented downwardly with respect to axis 24 and handpiece 25, it is readily apparent that other orientations (e.g., downwardly, to the right or left, or anywhere in between these directions) are possible. Indeed, a set of surgical instruments may be provided, each with a different bend region 18 orientation, to give the user maximum flexibility in determining the optimum bend configuration for a given surgical procedure other amounts of curvature can be provided.

Also, as described in the aforementioned patent application Ser. No. 07/634,599, now U.S. Pat. No. 5,152,744, pliable material (such as silicone rubber) may be disposed in slots 34 of inner tube 14. (Pliable material is illustrated in FIG. 2 by shaded area 150 within a slot 34 of inner tube 14.) The pliable material would further help avoid clogging by reducing the tendency of tissue fragments to become caught on the edges of slots 34 as the fragments pass through inner tube 14. Moreover, the pliable material is less compressible than empty space, and thus would serve to reduce the axial compressibility of flexible region 26.

A tube (made from, e.g., shrink wrap plastic) may be placed over outer tube in bend region 18 to cover slots 66. (A portion of such a tube 152 in shown in FIG. 2.) Among other advantages, a shrink wrap tube will avoid material becoming lodged within slots 66 and help prevent the edges of slots 66 (which may be sharp) from causing damage.

Surgical tools other than the cutting implement shown in the figures can be used. For example, the surgical tool need not have serrated edges and may alternatively be constructed as a bone abrading instrument. The surgical instrument can be constructed to perform procedures other than arthroscopy (such as laparoscopy).

Inner tube 14 may alternatively be flexible along its entire length so long as the tube is sufficiently stiff to transmit the forces applied to it (e.g., torsion) to surgical tool 11. For example, inner tubes 14 may comprise a nonmetal, such as plastic, and drive a separate, metal member that carries cutting implement 15. Such a configuration is shown in copending application Ser. No. 07/978,178, filed on Nov. 17, 1992, which is a continuation of application Ser. No. 07/600,531, filed on Oct. 19, 1990, which are both assigned to the present assignee and incorporated herein by reference.)

Figure 8:
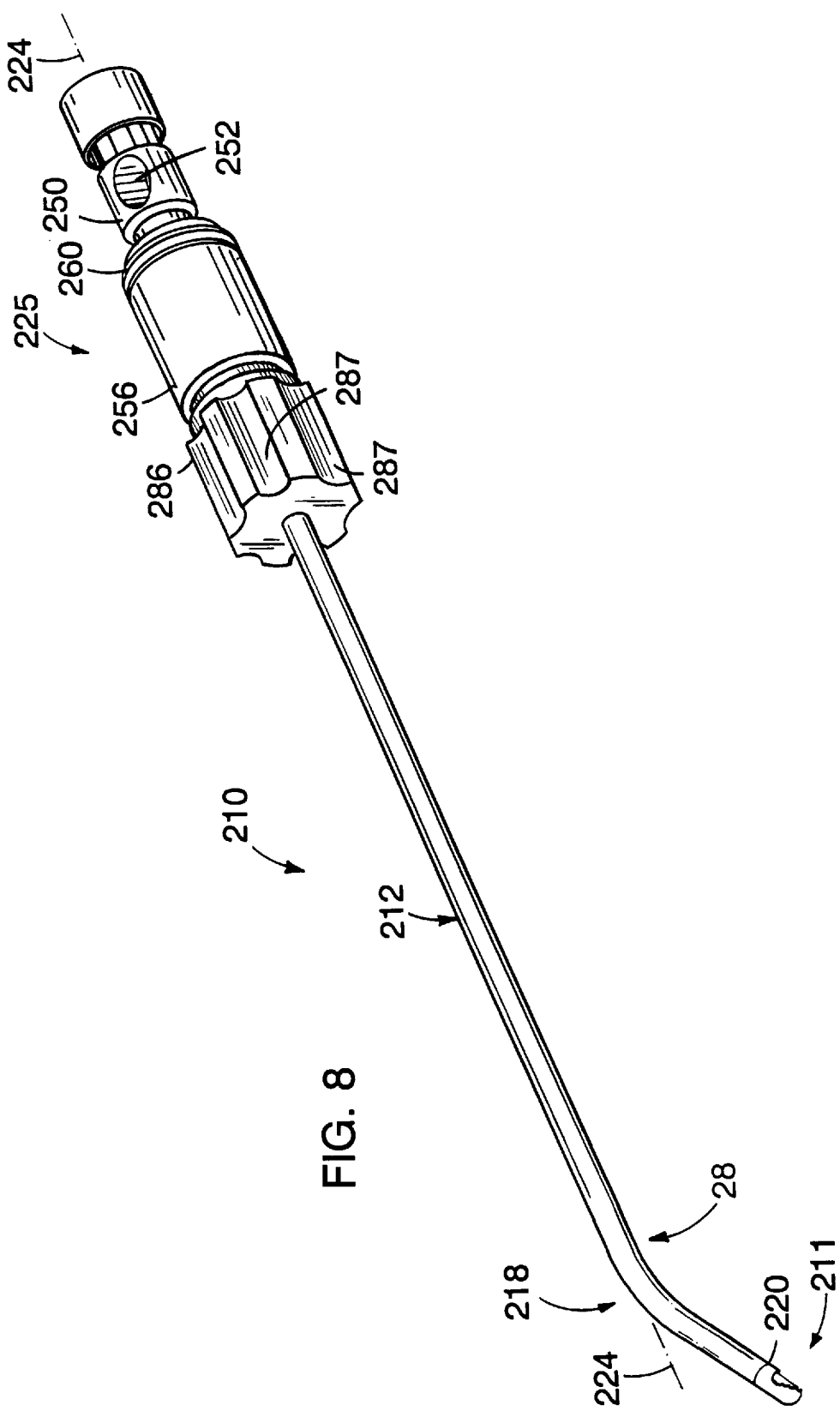
FIG. 8 shows another embodiment of a surgical instrument according to the invention.
Figure 9:
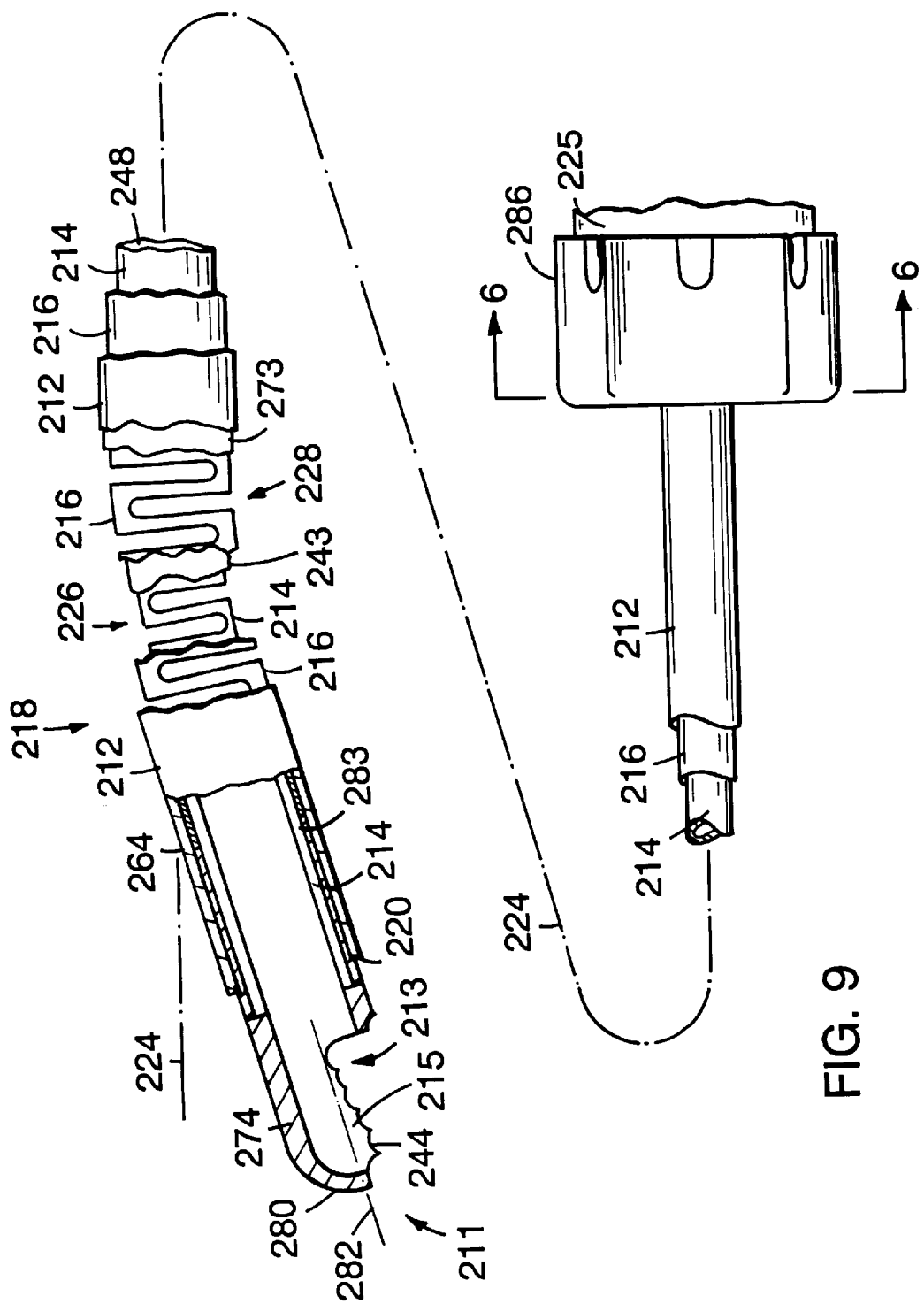
FIG. 9 is a partial cross-sectional view of portions of the instrument of FIG. 8, showing details of the tip and base.

A further embodiment of a surgical instrument in accordance with the invention is shown in FIGS. 8 and 9. Surgical instrument 210 includes a rigid outer tube 212, within which a surgical device is coaxially disposed. The surgical device, which carries a surgical tool 211 at its distal end, is comprised of a rotating, partially flexible inner tube 214, coaxially disposed within a partially flexible intermediate tube 216. Thus, whereas in the previously described embodiment the rigid member 16 was sandwiched between the two tubes 12, 14 comprising the surgical device, the surgical device of surgical instrument 210 is disposed coaxially within rigid outer tube 212.

The distal end of intermediate tube 216 includes an opening 213, the edges of which are sharpened and serrated, through which a cutting implement 215 (formed by sharpened, serrated edges of a similar opening in the distal end of inner tube 214) of surgical tool 211 is periodically exposed as inner tube 214 rotates. Outer tube 212 is curved through a bend region 218 disposed slightly proximally of the distal end 220 of outer tube 212 to offset surgical tool 211 angularly from a generally straight axis 224 of surgical instrument 210.

Tubes 212, 214, and 216 are proximally supported by a base 225 constructed of, e.g., polycarbonate plastic. As discussed in detail below, outer tube 212 mounts to a knob 286 of base 225, and intermediate tube 216 mounts to a hub 256 of base 225.

Inner tube 214 includes a slotted, flexible region 226 disposed within bend region 218 to accept the curvature imposed by bend region 218 and transmit torque (and other forces) applied at base 225 through bend region 218 to rotate cutting implement 215 with sufficient force to sever tissue or other body material exposed through opening 213. Intermediate tube 216 also has a slotted, flexible region 228 disposed within bend region 218 to accept the curvature imposed by bend region 218. (For clarity, in FIG. 9 inner tube 214 is not shown behind slotted, flexible region 228 of intermediate tube 216.) Flexible region 228 allows the relative rotational orientation between opening 213 and bend region 218 to be changed, without interfering with the ability of inner tube 214 to rotate within intermediate tube 216. As described in detail below, this feature enables the user to maintain surgical instrument 210 in an essentially fixed position, while rotationally varying the direction in which cutting is performed without changing the direction of offset of the bend region 218. Alternatively, the user can, without changing the direction in which cutting is performed, change the direction of offset of bend region 218.

Figure 10:
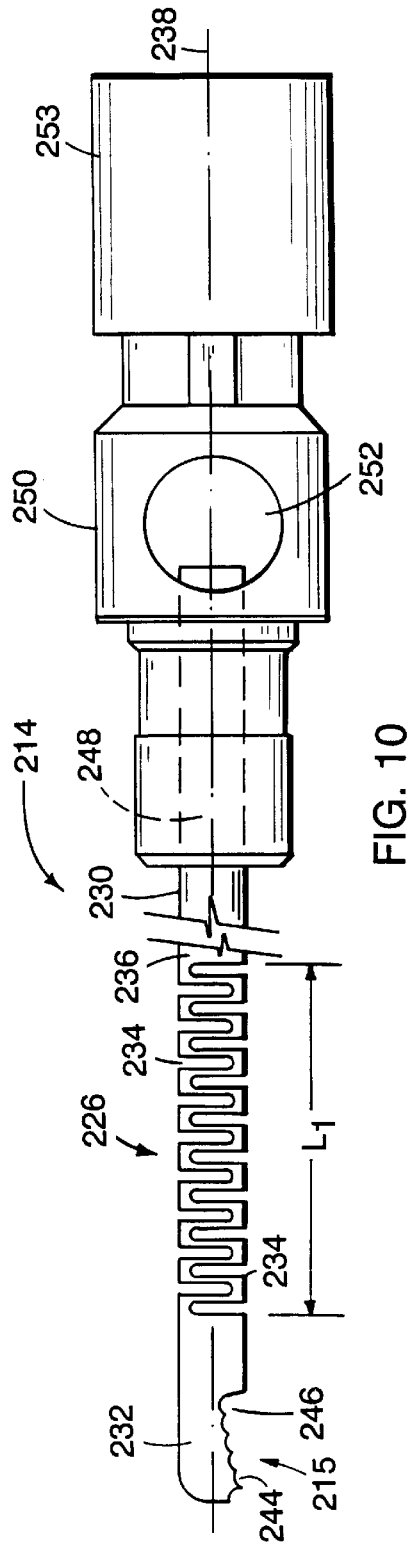

Referring also to FIG. 10, inner tube 214 is of generally the same construction as outer and inner tubes 12, 14 of the previously described embodiment. Rigid proximal and distal regions 230, 232 are connected by flexible region 226. Flexible region 226 is relieved with an axially extending series of circumferential slots 234 disposed in the walls 236 of tube 214, and is continuous with the adjacently disposed proximal and distal regions 230, 232. Each slot 234 is approximately 0.020 inches (0.508 mm) wide, and has a depth of about 0.135 inches (3.429 mm). The length $L_1$ of flexible region 226 should be sufficient (e.g. 0.70 inches, or 17.78 mm) that flexible region 226 spans the entire length of bend region 218.

A pliable sheath 243 (made from, e.g., heat-shrink tubing) slightly longer than $L_1$ is placed over inner tube 214 in bend region 218 to cover slots 234. (A portion of pliable sheath 243 in shown in FIG. 9.) Among other advantages, pliable sheath 43 helps prevent material from lodging within or passing through slots 234, and also helps prevent flexible region 226 from interfering with flexible region 228 as tubes 214, 216 rotate with respect to each other.

Distal region 232 of inner tube 214 supports cutting implement 215 (which is, for example, stainless steel and attached to tube 214 by welding or brazing). Cutting implement 215 is defined by serrated, sharpened edges 244 of a distal opening 246 in tube 214 and is sized to provide a close running fit with the interior surface of distal extension 274 of intermediate tube 216 (FIGS. 9 and 11) for efficient cutting. Opening 246 is an extension of a central aperture 248 in inner tube that runs the entire length of tube 214 (see also FIG. 9). After cutting implement 215 is attached to inner tube 214, the outer surface of the entire assembly is ground to a uniform outer diameter. Optionally, the outer surface of inner tube 214 may then be plated with silver to provide an improved friction surface between inner tube 214 and intermediate tube 216.

Proximal region 230 of inner tube 214 is mounted to a drive shaft 250 that rotates within base 225. Central aperture 248 terminates in a vacuum source opening 252 in drive shaft 250. The proximal end 253 of drive shaft 250 fits into a handpiece 310 (FIG. 14), which includes a motor 312 for rotating drive shaft 250 and inner tube 214 with respect to tubes 212 and 216. Opening 252 is coupled to a vacuum source 314 (FIG. 14) during operation to remove severed tissue and irrigating fluid from the surgical site via aperture 248 in a manner described in detail below.

Figure 11:
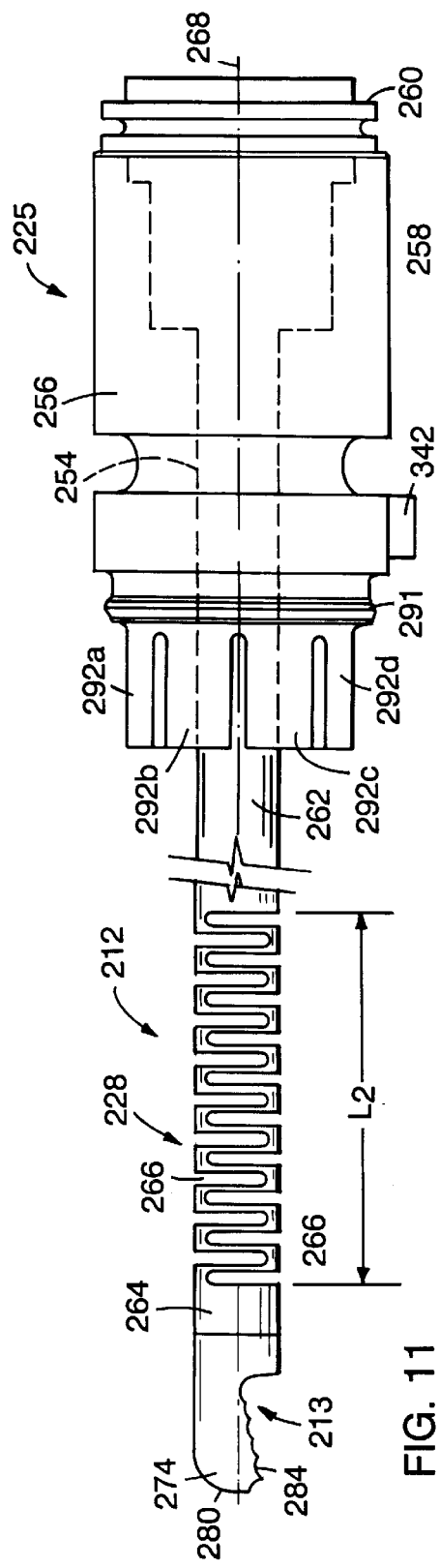

As shown in FIG. 11, intermediate tube 216 is hollow along its entire length to provide a passage 254 that receives inner tube 214 (FIG. 9). The proximal end of intermediate tube 216 is rigidly mounted, for example by ultrasonic welding, to a hub 256 of base 225. A cavity 258 in hub 256 communicates with passage 254 and is configured to receive drive shaft 250. During assembly, inner tube 214 is inserted through hub 256 into intermediate tube 216 (before bend region 218 is formed in outer tube 212). A pliable fitting 260 retains drive shaft 250 within hub 256. Fitting 260 further provides a fluid-tight seal when base 225 is inserted into handpiece 310.

Intermediate tube 216 is essentially a larger version of inner tube 214 and includes rigid proximal and distal regions 262, 264 that are integrally connected by flexible region 228. Flexible region 228 is relieved with an axially extending series of circumferential slots 266. Each slot 266 is approximately 0.025 inches (0.635 mm) wide and has a depth of about 0.140 inches (3.556 mm). The length $L_2$ of flexible region 228 should be sufficient (e.g. 0.70 inches, or 17.78 mm) that flexible region 228 spans the entire length of bend region 218. A pliable sheath 273 (made from, e.g., heat-shrink tubing) slightly longer than $L_2$ is placed over intermediate tube 216 in bend region 218 to cover slots 266. (A portion of pliable sheath 273 in shown in FIG. 9.)

To provide opening 213, a hollow, closed-ended distal extension 274 having the same outer diameter as intermediate tube 216 is secured to intermediate tube 216 at distal end 264. Extension 274 is, for example, stainless steel, and is welded or brazed to intermediate tube 216, which can be made of, for example, stainless steel.

Opening 213 is disposed in a distal tip 280 of extension 274 and faces somewhat to the side of intermediate tube 216. That is, opening 213 does not along its entire length extend completely to the centerline 282 of extension 274 (FIG. 9). As a result, while surgical tool 211 will cut tissue that enters opening 213 from the distal end of instrument 210, the majority of the cutting action is to one side. Moreover, the inner surface of tip 280 provides distal support for the rotating inner tube 214. The edges 284 of opening 213 are sharpened and serrated to cooperate with sharp edges 244 of cutting implement 215.

As shown in FIG. 9, when instrument 210 is assembled, a slight gap 283 exists between the outer diameter of inner tube 214 and the inner diameter of intermediate tube 216. The gap 283 accommodates the thickness of pliable sheath 243 covering flexible region 226. Extension 274, however, has a reduced inner diameter with respect to the remainder of intermediate tube 216, such that the clearance between cutting implement 215 and the inner diameter of extension 274 is small (e.g., approximately 0.002 inches, or 0.051 mm). This arrangement maintains the close-running fit between edges 244, 284 while allowing inner tube 214 to rotate freely. The essentially identical inner diameters of extension 274 and inner tube 214 avoid cutting implement 215 scoring or seizing as it rotates.

FIG. 12 shows the rigid member, outer tube 212 (before bend region 218 is formed), which is made from a rigid material such as metal (e.g., stainless steel). Proximal region 285 of outer tube 212 is rigidly secured, for example by ultrasonic welding, to a knob 286 at a sealed joint. A shoulder 289 on the inner surface of the proximal end of knob 286 engages a mating shoulder 291 on the outer surface of the distal end of hub 256 (FIG. 11), such that knob 286 rotatably mounts to hub 256 (see also FIG. 9). Thus, the relative rotational orientation between knob 286 and hub 256 can be changed, e.g., by grasping knob 286 and rotating hub 256, or by grasping hub 256 and rotating knob 286. The attachment mechanism connecting knob 286 and hub 256 is described in further detail below. Knob 286 is provided with a series of circumferentially spaced indentations 287 that facilitate the user's efforts manually to manipulate knob 286.

A central passage 288 extends through outer tube 212 and knob 286 to receive intermediate tube 216 and inner tube 214, which protrude through the open distal end 220 of outer tube 212. The inner diameter of outer tube 212 exceeds the outer diameter of intermediate tube 216 by a sufficient amount to accommodate pliable sheath 273 covering flexible region 228 (e.g., by approximately 0.005 inches, or 0.128 mm). This allows the user to change the relative rotational orientation between intermediate tube 216 and outer tube 212, but avoids excessive play or wobble between the intermediate and outer tubes 212, 216. After intermediate tube 216 is inserted into outer tube 212 and inner tube 214 is inserted into intermediate tube 216, outer tube 212 is curved to provide bend region 218 (FIG. 8).

When knob 286 is grasped firmly and hub 256 rotated, the rotational orientation of outer tube 212, and thus the direction of offset of bend region 218, remains fixed. Because proximal portion 262 of intermediate tube 216 is mounted to hub 256, rotating hub 256 also rotates intermediate tube 216 within outer tube 212. Intermediate tube 216 communicates this torque applied by the user at the base to extension 274 through flexible region 228 disposed in bend region 218. Thus, as hub 256 is rotated with respect to knob 286, the direction of offset of bend region 218 remains fixed, but opening 218 in extension 274 rotates with respect to bend region 218.

Alternatively, when hub 256 is grasped firmly and knob 288 is rotated, the directional orientation of opening 213 remains fixed (because hub 256 is also fixed), and the direction of offset of bend region 218 rotates (because knob 286 and outer tube 212 rotate). As the direction of offset of bend region 218 rotates, flexible region 228 allows the direction of offset of distal region 264 of intermediate tube 216 to rotate also.

Referring to FIGS. 11 and 13 (FIG. 13 for clarity does not show tubes 214 and 216 in cross-section), the interior of knob 286 is octagonal in cross-section, its inner surface being composed of eight flat surfaces 290a–h of equal width. Cantilevered from the distal end of hub 256 are eight distally projecting flexible fingers 292a–h spaced by equal amounts (i.e., 45°) around the circumference of shoulder 291. Fingers 292a–h lie perpendicular to longitudinal axis 268 of intermediate tube 216. Each of fingers 292a–h is an irregular pentagon in cross-section, such that when knob 286 is assembled onto hub 256, the radial outermost point 294a–h of each finger 292a–h rests in an apex formed by the intersection of adjacent flat surfaces 290a–h.

Fingers 292a–h and flat surfaces 290a–h coact to allow the relative rotational orientation between knob 286 and hub 256 to be changed, in a ratchet-like fashion, in discrete, 45° steps. As the relative rotational orientation changes (i.e., as the knob 286 and hub 256 rotate with respect to one another), outermost points 294a–h move across flat surfaces 290a–h, initially forcing fingers 292a–h radially inward. When outermost points 294a–h move past the respective midpoints of the surfaces 290a–h, the elastic energy stored in the displaced flexible fingers 292a–h forces the fingers radially outward until relative rotational orientation between knob 286 and hub 256 has changed by 45°, and fingers 292a–h rest in the adjacent apex. Thus, fingers 290a–h positively urge outermost points 294a–h into each associated apex as it is encountered, thereby giving the surgeon kinesthetic feedback as to the amount by which opening 213 has been rotated, and helping to avoid accidental rotation of outer tube 212 with respect to hub 256.

Figure 14:
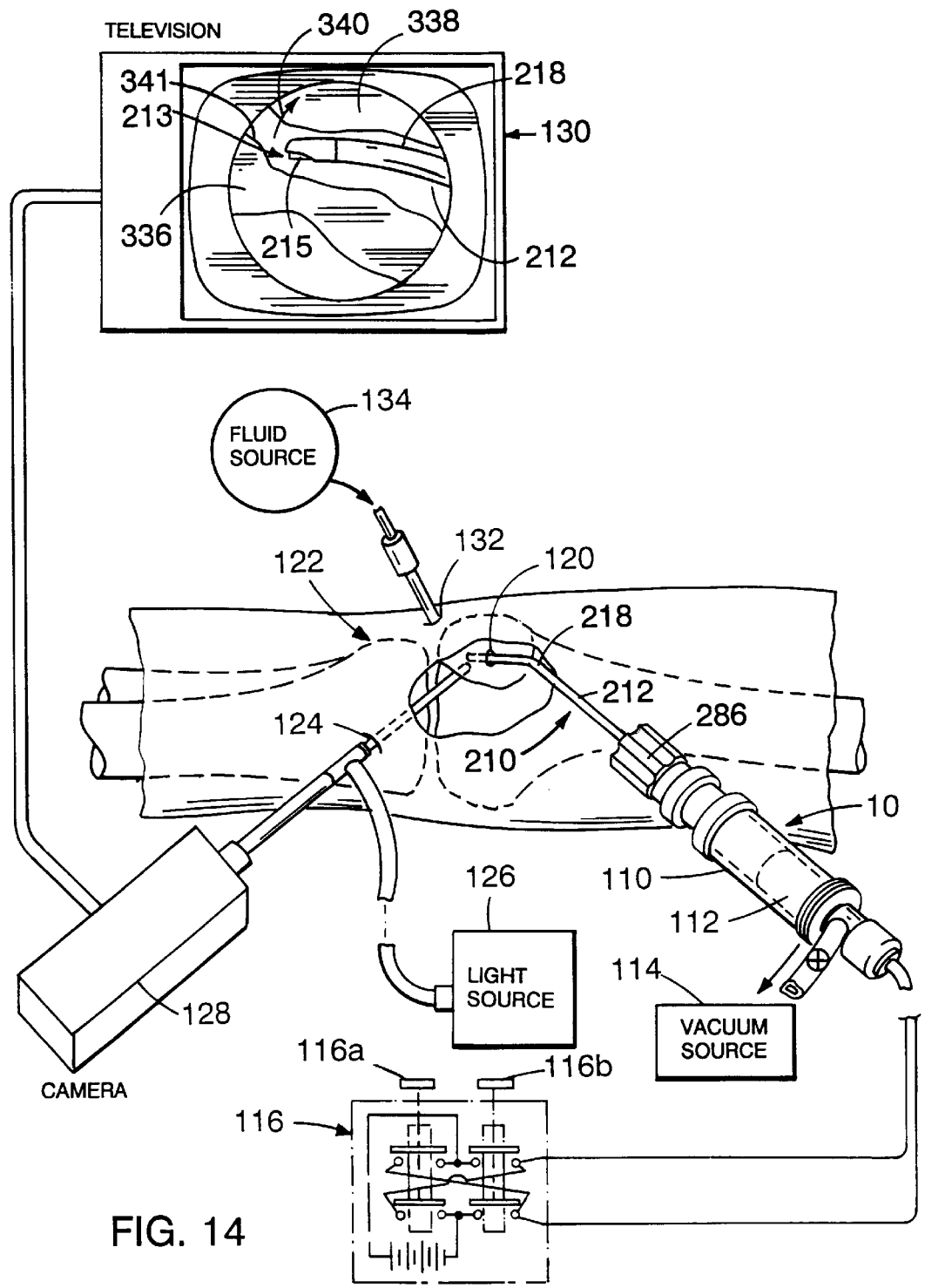
FIG. 14 shows the surgical instrument of FIG. 8 in use.

Referring also to FIG. 14, in operation surgical instrument 210 is employed similarly to surgical instrument 10, as described in connection with FIG. 7.

As described, fluid introduced through a third puncture wound 132 from a fluid source 134 distends the body joint and irrigates the site, rendering tissue 136 (which is, e.g., synovial tissue) mobile so that it floats and can be displaced (similar to the movement of seaweed in water). Note that synovial tissue 336 is located beneath outer tube 212; thus, the rotational orientation between knob 286 and hub 256 is selected to produce the desired orientation between the bend region 218 and opening 213 (FIGS. 9 and 13). The curvature provided by bend region 218 allows surgical instrument 210 to be easily positioned to place surgical tool 211 against tissue 336 (even if tissue 336 is located in a region of the joint that cannot easily be reached by a straight-shafted instrument) without manipulating instrument 210 unduly or requiring that additional punctures be made to gain access to tissue 336. This reduces patient discomfort, as well as the chances for infection and other deleterious consequences of the surgery.

The surgeon progressively cuts away synovial tissue 336 by moving surgical instrument 210 from side to side and in the axial direction using handpiece 310 (while viewing television screen 130). If during the procedure the surgeon wishes to cut tissue from another region of the synovial tissue, the present invention allows him to do so simply by changing the relative rotational orientation between surgical tool opening 213 and bend region 218.

For example, if the surgeon wishes to remove tissue from region 338 located above outer tube 212 (e.g., in the direction of arrow 340), he grasps knob 286 with the finger and thumb of one hand and turns handpiece 110, which in turn rotates hub 256. Handpiece 110 is provided with a distinct protuberance (not shown) that points in the same direction as tab 342 on hub 256 (FIG. 11) and opening 213 in surgical tool 211. Thus, the surgeon would continue to grasp knob 286 and rotate handpiece 110 until he actually senses from the handpiece protuberance that opening 213 is properly oriented. The rotational force applied by the surgeon is transmitted through bend region 218 by flexible region 228, thereby causing distal extension 274 of intermediate tube 216 to rotate with respect to outer tube 212, changing the rotational orientation of opening 213 with respect to bend region 218 (in this case, by 180°).

Alternatively, if for example the surgeon wishes to change the direction of offset of bend region 218 without changing the direction of opening 213 (and thus the cutting direction of surgical tool 211), e.g. to remove tissue from region 341, he grasps handpiece 110 and rotates knob 286 with the finger and thumb of one hand. When the direction of offset of bend region 218 is as desired (in this case, when it had been rotated by 180°), the surgeon then moves the entire instrument axially until opening 213 was adjacent to region 341.

The surgeon can change the relative rotational orientation between bend region 218 and opening 213 at any time. For example, inner tube 214 can be driven by motor 112 or may be stationary while the surgeon rotates opening 213. Distal extension 274 rotates smoothly with respect to the stationary outer tube 212, while providing constant distal support (at tip 280) for rotating inner tube 214. The surgeon can return to cutting tissue 336 at any time simply by rotating handpiece 310 in either direction while holding knob 286 fixed (if the surgeon had been cutting from region 338), or by rotating knob 286 in either direction while holding handpiece 110 fixed (if the surgeon had been cutting from region 341).

Tissue fragments and other body material cut by surgical tool 211 are withdrawn from the surgical site along with irrigation fluid via central aperture 248 of inner tube 214 (FIG. 9) in response to suction applied by vacuum source 114. Flexible sheath 243 covering inner tube 214 ensures that tissue fragments, irrigation fluid, and other material do not pass through slots 234, thereby assisting in the transport of tissue fragments through the chamber and out of surgical instrument 210.

Although surgical instrument 210 is shown with opening 213 aligned in the same direction as tab 342 on hub 256 (FIG. 11), it is readily apparent that other alignments (e.g., in the opposite direction, to the right or left, or anywhere in between these directions) are possible. Indeed, a set of surgical instruments may be provided, each with a different opening 213 orientation, to give the user maximum flexibility in determining the optimum configuration for a given surgical procedure. In addition, outer tube 212 can be curved to any desired degree.

Surgical tools other than the cutting implement shown in the figures can be used. For example, the surgical tool can be configured to cut tissue exposed to distal tip 280 of intermediate tube 216. In this end cutter embodiment, coacting cutting edges are provided at the distal tips of both the inner and the intermediate tubes, and an axial bearing maintains the respective edges in close cutting relationship. Further, axial force can be used instead of, or in addition to, torque to operate the surgical tool. For example, the surgical tool could be a hinged punch or jaw assembly operated by an axial force applied at hub 256.

Referring to FIGS. 15–19, the hub and knob of surgical instrument 400 are constructed to allow the user to temporarily lock the instrument in any selected rotational orientation to avoid accidental rotation.

Surgical instrument 400 includes a rigid outer tube 412, within which a surgical device is coaxially disposed. The surgical device, which carries a surgical tool 411 at its distal end, is comprised of a rotating, partially flexible inner tube (the inner tube is similar in construction to inner tube 214 of FIG. 10 and thus is not shown in FIGS. 15–19), coaxially disposed within a partially flexible intermediate tube 416 (which is similar in construction to intermediate tube 216 of FIG. 11 and thus is only partially shown in FIG. 16).

The distal end of intermediate tube 416 includes an opening 413, the edges of which are sharpened and serrated, through which a cutting implement, not shown (formed by sharpened, serrated edges of a similar opening in the distal end of the inner tube), of surgical tool 411 is periodically exposed as the inner tube rotates. Outer tube 412 is curved through a bend region 418 disposed slightly proximally of the distal end 420 of outer tube 412 to offset surgical tool 411 angularly from a generally straight axis 424 of surgical instrument 400.

Outer tube 412, intermediate tube 416, and the inner tube are proximally supported by a base 425 constructed of, e.g., polycarbonate plastic. As discussed in detail below, outer tube 412 is mounted to a knob 430 of base 425, and intermediate tube 416 is mounted to a hub 432 of base 425. Hub 432 includes a latch 433 for securing base 425 within a motorized handpiece. (Latch 433 and the motorized handpiece with which surgical instrument 400 is used are described in a copending patent application entitled "Surgical Instrument Handpiece and System," by Douglas Sjostrom et al., filed on Apr. 10, 1996, assigned to the present assignee, and incorporated herein by reference.) A drive shaft 434 connected to the proximal end of the inner tube is rotatably received by hub 432, as in the above-described embodiments. The proximal end of drive shaft 434 fits into the handpiece, the motor of which rotates drive shaft 434 and the inner tube with respect to tubes 412 and 416.

Figure 15:
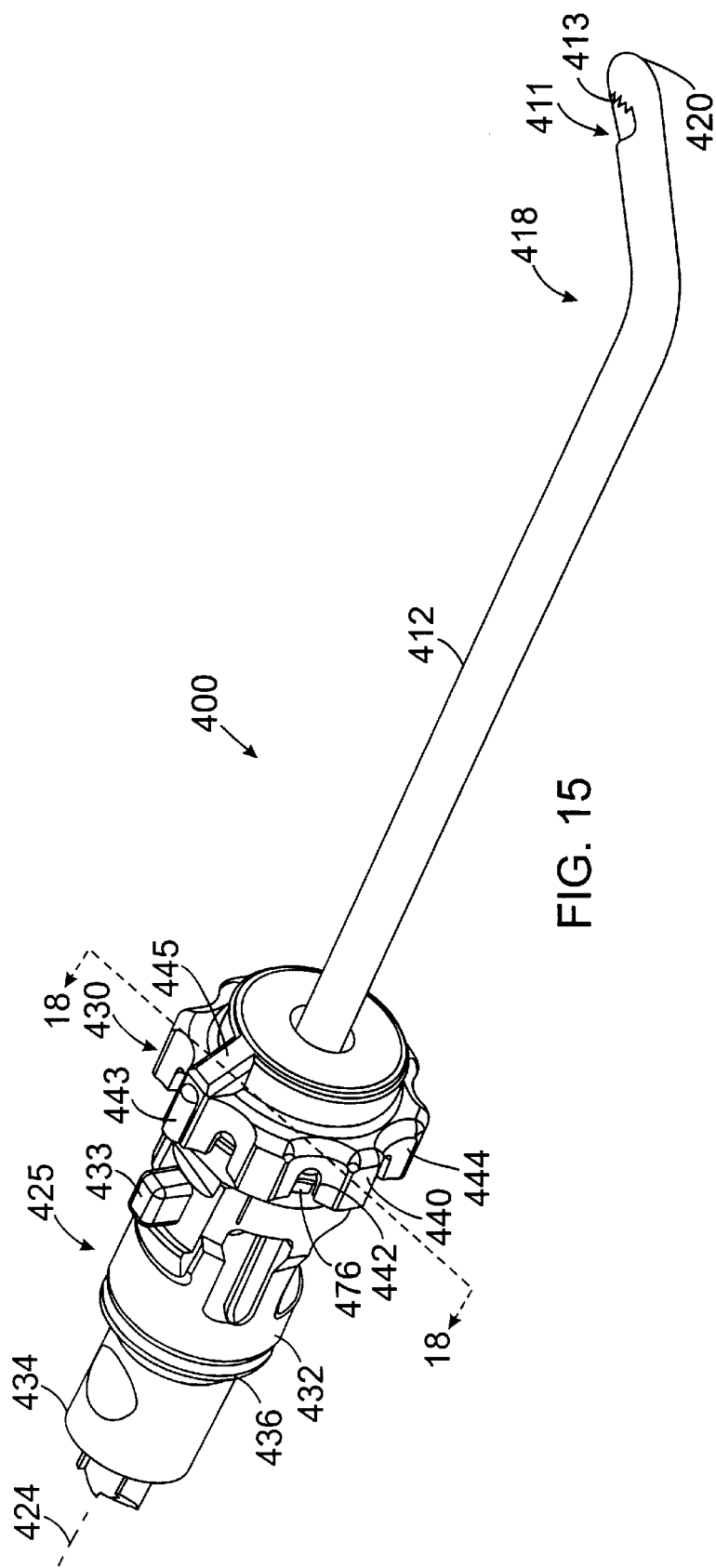
FIG. 15 shows another embodiment of a surgical instrument according to the invention.
Figure 16:
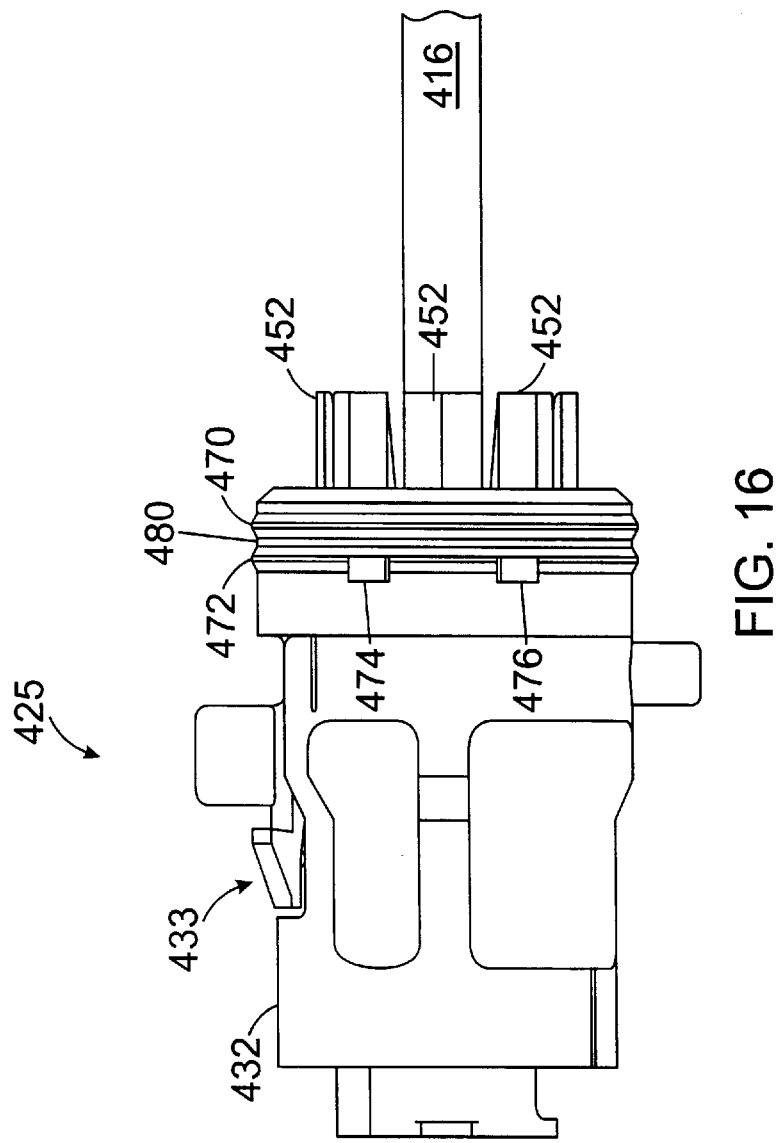

As shown in FIG. 16, intermediate tube 416 is hollow along its entire length to provide a passage that receives the inner tube. The proximal end of intermediate tube 416 is rigidly mounted, for example by ultrasonic welding, to hub 432 of base 425. A cavity (note shown) in hub 432 communicates with the passage and is configured to receive drive shaft 434. During assembly, the inner tube is inserted through hub 432 into intermediate tube 416 (before bend region 418 is formed in outer tube 412). A fitting 436 on the proximal end of hub 432 (FIG. 15) helps retain drive shaft 434 within hub 432 and provides a fluid-tight seal when base 425 is inserted into the handpiece.

FIG. 17 shows a portion of outer tube 412 (before bend region 418 is formed), which is made from a rigid material such as metal (e.g., stainless steel). The proximal end of outer tube 412 is rigidly secured, for example by ultrasonic welding, to knob 430 at a sealed joint. Knob 430 includes a set of (e.g., eight) proximally extending, cantilevered arms 440. Arms 440 are circumferentially spaced by a set of U-shaped slots 442 to define an opening which receives the distal end of hub 432. Indentations 444 are provided in the surface of knob 430 between arms 440 to facilitate the user's efforts manually to manipulate knob 430. A rib 443 is formed on the exterior surface of one arm 440 (e.g., an arm 440 oriented at a selected angle with respect to the direction of bend region 418) and an angled fin 445 extends from that arm 440 toward the distal end of knob 430 to allow the user to tactilely sense the orientation of the bend.

Knob 430 is rotatably mounted to hub 432 with arms 440 so that the relative rotational orientation between knob 430 and hub 432 can be changed, e.g., by grasping knob 430 and rotating hub 432, or by grasping hub 432 and rotating knob 430. The rotational operation of instrument 400 is the same as that of instrument 210, described above. The attachment mechanism connecting knob 430 and hub 432 is described in further detail below.

As with surgical instrument 210 (FIG. 8) a central passage extends through outer tube 412 and knob 430 to receive intermediate tube 416 and the inner tube (which protrude through an open distal end of outer tube 412). The inner diameter of outer tube 412 exceeds the outer diameter of intermediate tube 416 by a sufficient amount to accommodate a pliable sheath (not shown) covering the flexible region of the intermediate tube (see FIG. 9). This allows the user to change the relative rotational orientation between intermediate tube 416 and outer tube 412, but avoids excessive play or wobble between the intermediate and outer tubes 412, 416. After intermediate tube 416 is inserted into outer tube 412 and the inner tube is inserted into intermediate tube 416, outer tube 412 is curved to provide bend region 418 (FIG. 15).

Figure 18:
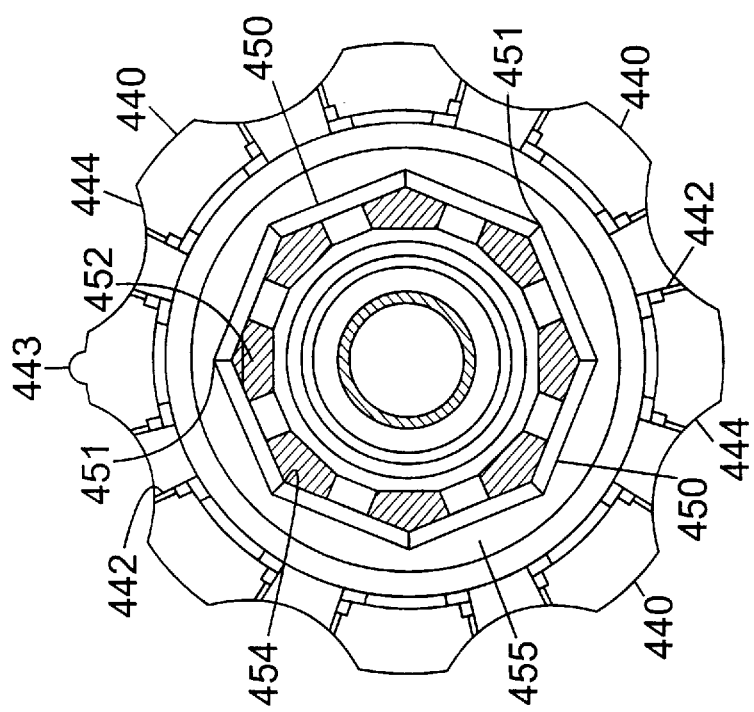
FIG. 18 is a cross-section of the surgical instrument, taken along line 18—18 of FIG. 15.

Referring to FIGS. 16 and 18 (FIG. 18 for clarity does not show the inner and intermediate tubes in cross-section), the interior of knob 430 includes a flat shoulder 455 which defines an octagonally-shaped cavity. The eight surfaces 450 bounding the cavity are flat and have equal widths. Each arm 440 is centered about the apex 451 formed by the intersection between adjacent surfaces 450. Cantilevered from the distal end of hub 432 are eight distally projecting flexible fingers 452 spaced by equal amounts (i.e., 45°) around the circumference of hub 432. Fingers 452 lie parallel to the longitudinal axis of intermediate tube 416. Each of fingers 452 is triangular in cross-section, such that when knob 430 is assembled onto hub 432, the radial outermost point 454 of each finger 452 rests in apex 451 formed by the intersection of adjacent flat surfaces 450. Fingers 452 are slightly compressed by their engagement with surfaces 450.

Fingers 452 and flat surfaces 450 coact to allow the relative rotational orientation between knob 430 and hub 432 to be changed, in a ratchet-like fashion, in discrete, 45° steps. As the relative rotational orientation changes (i.e., as knob 430 and hub 432 rotate with respect to one another), outermost points 454 move across flat surfaces 450, initially forcing fingers 452 radially inward. Note that during rotation, knob 430 and hub 432 are in continuous engagement with each other due to the interaction of cantilevered fingers 452 and surfaces 450. When outermost points 454 move past the respective midpoints of the surfaces 450, the elastic energy stored in the displaced flexible fingers 452 forces the fingers radially outward until relative rotational orientation between knob 430 and hub 432 has changed by 45°, and fingers 452 rest in the adjacent apex 451. Thus, fingers 450 positively urge outermost points 454 into each associated apex 451 as it is encountered, thereby giving the surgeon kinesthetic feedback as to the amount by which opening 413 (FIG. 15) has been rotated, and helping to avoid accidental rotation of outer tube 412 with respect to hub 432.

Referring in particular to FIG. 16, a pair of axially spaced, circumferential ridges 470, 472 are arranged on the exterior of hub 432 proximally of fingers 452. Two pairs of spaced tabs 474, 476 protrude from the exterior surface of hub 432 on the proximal side of ridge 472. Only one pair of tabs 474, 476 is shown; the other pair is spaced by 180 degrees from the pair shown along the circumference of hub 432. Each pair of tabs is centered about one of fingers 452 of hub 432, and the spacing between tabs 474, 476 is approximately equal to the width of each arm 440 on knob 430. As a result, whenever knob 430 and hub 432 are in one of the eight ratcheted rotational positions, two arms 440 of knob 430 are positioned between the two pairs of tabs 474, 476.

Referring also to FIG. 17, a radially projecting boss 478 is disposed on the interior surface of each arm 440 of knob 430, at the proximal end of arm 440. When knob 430 is assembled onto hub 432, bosses 478 of arms 440 snap fit within an annular groove 480 between ridges 472, 474. Arms 440 are sufficiently flexible to expand outwardly and then return to their original position as bosses 478 are passed over ridge 470. Bosses 478 travel within annular groove 480 when knob 430 and hub 432 are rotated with respect to each other as described above. The compression of fingers 452 against octagonal surfaces 450 develops an distally-directed force away from hub 432. This force urges knob 430 distally, thereby urging bosses 478 against ridge 470 and avoiding accidental movement of knob 430 into the locked position.

When the user wishes to temporarily lock knob 430 and hub 432 in a selected rotational orientation, the user slides knob 430 axially and proximally with respect to hub 432 to urge bosses 478 over ridge 472. This movement causes the knob arms 440 which are positioned between pairs of tabs 474, 476 to be axially repositioned between tabs 474, 476. As a result, these arms 440 are rotationally captured between the pairs of tabs 474, 476, thereby locking knob 430 non-rotatably in position on hub 432. That is, if the user attempts to turn knob 430 or hub 432 when knob 430 is in the locked position, each pair of tabs 472, 474 are engaged by a pair of adjacent arms 440, preventing rotational movement.

Figure 19:
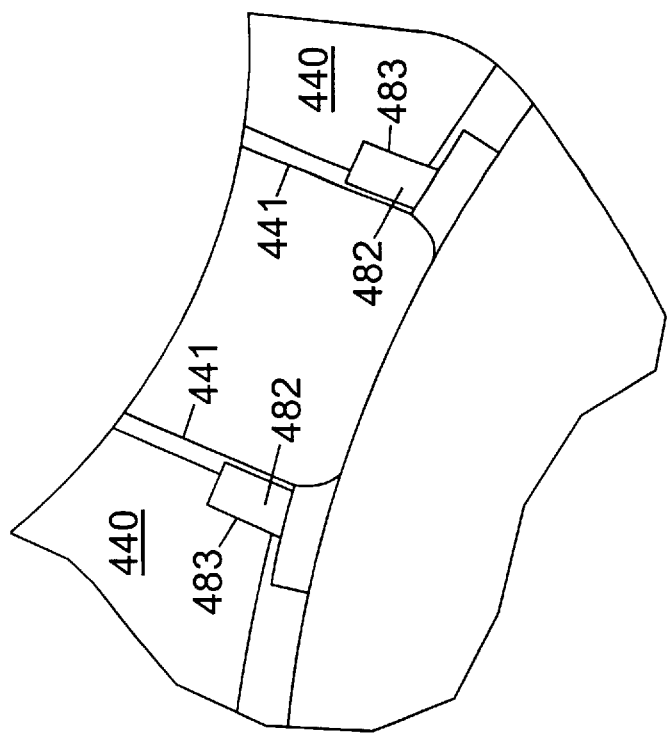
FIG. 19 is an enlargement of a portion of the knob of FIG. 18.

Referring also to FIG. 19, each arm 440 of knob 430 includes a pair of flat-faced notches 482 (the notches 482 of adjacent arms 440 are shown in FIG. 19). Unlike the sides 441 of arms 440 (which are inclined slightly with respect to the longitudinal axis of the instrument), the side surfaces 483 of notches 482 are parallel to the side surfaces of tabs 474, 476. As a result, tabs 472, 474 are engaged by flat, non-inclined surfaces 483 to resist rotation more reliably than if inclined sides 441 were to engage tabs 474, 476.

The axial motion of knob 430 is limited by the engagement of the distal tips of fingers 452 against the interior surface 455 (Fib. 18) of knob 430. At this point, bosses 478 are positioned on the proximal side of ridge 472 and are still slightly expanded by ridge 472. This helps prevent knob 430 from accidentally slipping back to the unlocked position. When the user wishes to unlock knob 430, he or she simply slides knob 430 axially and distally. Ridge 472 is slightly smaller in diameter than ridge 470, and thus bosses 478 are relatively easily urged over ridge 472 into groove 480. The increased diameter of ridge 470 helps avoid knob 430 being moved too far distally and disassembled from hub 432.

Although the locking feature has been described with a surgical instrument 400 similar to that shown in FIG. 8 (i.e., surgical instrument 210) the locking feature may also be implemented with surgical instrument 10 (FIG. 1).

The locking feature may also be used in a two-tube instrument in which an outer tube with a distal tissue-admitting opening is rotatably mounted to a hub and an inner tube rotates within the outer tube so that a cutting implement at the distal end of the inner tube cuts tissue admitted through the opening. One example of such an instrument is shown in U.S. Pat. No. 5,376,078 issued to Dinger and incorporated herein by reference.

Referring to FIG. 20, an example of such a two-tube instrument 500 is shown. (In this example, like reference numerals will be used to identify components that are similar to the components of instrument 400 discussed above.) Instrument 500 includes a rigid outer tube 502 the proximal end of which is attached to knob 430. Outer tube 502 extends distally through a bend region 504 to a distal end 506 in which a tissue-admitting opening 508 with sharpened edges is located. An inner tube 510 (shown in phantom) extends with a close running fit through outer tube 502 to the distal end of instrument 500. The proximal end of inner tube extends through hub 432 of base 425 and is secured to drive shaft 434. The distal end 512 of inner tube defines any of the cutting implements discussed above. Inner tube 510 is rendered flexible in bend region 524 using, e.g., any of the configurations discussed herein.

Note that neither of tubes 502, 510 is secured to hub 432. Instead, hub 432 serves as a support for knob 430 and drive shaft 434. Thus, rotating knob 430 with respect to hub 432 causes outer tube 502 and opening 508 to rotate about the axis of instrument 500, thereby changing the instrument's angle of cutting attack. The locking feature with which knob 430 and hub 432 are equipped allows outer tube 502 and opening 508 to be temporarily locked in any selected rotational orientation as discussed above.

Still other embodiments are possible. For example, the rotatable engagement between knob 430 and hub 432 can be provided by a friction fit between these elements, rather than by the resilient contact described above.

While the invention has been described in terms of surgical instruments for arthroscopy, the invention may also be used with other types of instruments, for example, instruments configured for other kinds of endoscopic procedures and for biopsy applications.

What is claimed is:

1. A surgical instrument comprising
   a first member extending distally from a proximal end and having an opening in a distal region for admitting tissue,
   a second member disposed within said first member for moving a cutting implement and causing it to cut tissue that is exposed to said implement through said opening,
   a hub, and
   a knob attached to said proximal end of said first member, said knob being mounted in rotatable engagement with said hub so that said knob can be selectively rotated to a plurality of discrete positions while remaining in interengagement with said hub to rotate said first member and selectively change a rotational orientation of said opening with respect to said hub, thereby to allow said opening to be selectively positioned to a corresponding plurality of discrete rotational orientations,
   wherein said hub includes a plurality of flexible cantilevered fingers each of which corresponds to one of said discrete positions, said knob having a plurality of mating regions, each of said mating regions engaging one of said fingers during rotation of said knob to maintain said selective positioning of said opening in one of said discrete rotational orientations,
   said knob being axially movable with respect to said hub to a locked position in which said knob nonrotatably engages said hub.

2. The instrument of claim 1 wherein said hub includes a ridge on an exterior surface thereof, said knob including a resilient member which engages said ridge when said knob is axially moved to said locked position.

3. The instrument of claim 2 wherein said knob comprises a plurality of said resilient members circumferentially spaced to define an opening in which a portion of said hub is disposed, said ridge being circumferentially arranged around said portion of said hub.

4. The instrument of claim 3 wherein each of said resilient members includes a radial projection which engages said ridge when said knob is axially moved to said locked position.

5. The instrument of claim 4 further comprising a second annular ridge arranged around said portion of said hub and axially spaced from the first mentioned ridge, said radial projections of said resilient members being axially disposed between said ridges when said knob is in rotatable engagement with said hub.

6. A surgical instrument disposed generally along an axis, said surgical instrument comprising a first member extending distally from a proximal end and having a bend region that angularly offsets a distal end of said first member from an axis of said first member, a second member having a proximal end mounted to a hub and extending coaxially with said first member to a distal end disposed distally of said bend region, said second member having an opening at said distal end for admitting tissue, a cutting implement movable with respect to said second member and disposed to cut tissue exposed through said opening, and a knob attached to said proximal end of said first member, said knob being mounted in rotatable engagement with said hub to rotate said first member and thereby selectively change a rotational orientation of said bend region with respect to said hub, said knob being axially movable with respect to said hub to a locked position in which said knob nonrotatably engages said hub.

7. The instrument of claim 6 wherein said knob is axially movable in an opposite direction from said locked position to restore said rotatable engagement between said knob and said hub.

8. The instrument of claim 7 wherein said hub includes a plurality of said protrusions disposed to engage a plurality of said portions of said knob when said knob is axially moved to said locked position.

9. The instrument of claim 7 wherein said knob comprises a plurality of members circumferentially spaced to define an opening in which a portion of said hub is disposed, each of said members having a selected width, said hub including a pair of said protrusions spaced by said width so that one of said members is positioned between said pair of protrusions when said knob is axially moved to said locked position.

10. The instrument of claim 9 further comprising a second pair of said protrusions spaced from each other on said hub by said selected width.

11. The instrument of claim 9 wherein said one of said members includes a notch configured to receive a said protrusion when said knob is axially moved to said locked position.

12. The instrument of claim 6 wherein said hub includes a protrusion which is axially spaced from a portion of said knob when said knob is in rotatable engagement with said hub, said protrusion being disposed to engage said portion of said knob when said knob is axially moved to said locked position.

13. The instrument of claim 6 wherein said second member includes a flexible region in said bend region.

14. The instrument of claim 13 wherein said second member is disposed within said first member and extends through an open distal end of said first member.

15. The instrument of claim 13 wherein said first member is disposed within said second member.

16. The instrument of claim 6 further comprising a third ember disposed coaxially with said first member and said second member, said third member being operatively connected to said cutting implement to move said cutting implement and cause it to cut tissue that is exposed to said implement through said opening.

17. The instrument of claim 16 wherein said third member includes a flexible region in said bend region.

* * * * *

UNITED STATES PATENT AND TRADEMARK OFFICE
CERTIFICATE OF CORRECTION

PATENT NO. : 5,833,692
DATED : November 10, 1998
INVENTOR(S) : Peter M. Cesarini et al.

It is certified that error appears in the above-identified patent and that said Letters Patent is hereby corrected as shown below:

On the title page, item [56] add the following:

--4,445,509   05/1984   Auth--

Col. 14, line 7, replace "actually" with --tactually--.

Col. 20, claim 16, line 32, replace "ember" with --member--.

Signed and Sealed this

Twenty-seventh Day of July, 1999

Attest:

Q. TODD DICKINSON

Attesting Officer

Acting Commissioner of Patents and Trademarks